United States Patent [19]
Wybourne et al.

[11] Patent Number: 5,465,151
[45] Date of Patent: Nov. 7, 1995

[54] SENSORS EMPLOYING INTERFERENCE OF ELECTROMAGNETIC WAVES PASSING THROUGH WAVEGUIDES HAVING FUNCTIONALIZED SURFACES

[75] Inventors: Martin N. Wybourne; John F. W. Keana, both of Eugene, Oreg.; Sui X. Cai, Irvine, Calif.; Mingdi Yan; Jong Wu, both of Eugene, Oreg.

[73] Assignee: State of Oregon Acting By and Through the State Board of Higher Education on Behalf of The University of Oregon, Eugene, Oreg.

[21] Appl. No.: 14,425

[22] Filed: Feb. 5, 1993

Related U.S. Application Data

[63] Continuation-in-part of Ser. No. 6,453, Jan. 21, 1993.
[51] Int. Cl.$^6$ ..................................... G01B 9/02
[52] U.S. Cl. ........................... 356/361; 356/345; 385/14
[58] Field of Search .................... 356/361, 345; 250/227.14, 227.19; 422/82.05, 82.06, 82.11, 83, 86, 91; 435/805; 436/164; 385/12, 14

[56] References Cited

U.S. PATENT DOCUMENTS

| | | |
|---|---|---|
| 3,205,206 | 9/1965 | Marcantonio . |
| 3,211,713 | 10/1965 | Breslow . |
| 3,284,421 | 11/1966 | Breslow . |
| 3,888,833 | 6/1975 | Lednicer et al. . |
| 4,007,089 | 2/1977 | Smith, III . |
| 4,309,453 | 1/1982 | Reiner et al. . |
| 4,654,292 | 3/1987 | Oie et al. . |
| 4,950,074 | 8/1990 | Fabricius et al. ............. 356/361 |
| 5,002,582 | 3/1991 | Guire et al. . |
| 5,120,130 | 6/1992 | Lukosz ......................... 356/361 |
| 5,173,747 | 12/1992 | Boianski et al. ............. 356/361 |
| 5,262,842 | 11/1993 | Gauglitz et al. ............. 356/361 |

OTHER PUBLICATIONS

Seferis, "Refractive Indices of Polymers," in Brandrup et al. (eds.) *Polymer Handbook*, 3d ed., pp. VI–451–VI/461, Wiley (1989).

Saavedra et al., "Prism Coupling into Polymer Integrated Optical Waveguides with Liquid Superstrates," *Appl. Spectroscopy* 44:1210–1212 (1990).

Saavedra et al., "In Situ Quantification of Protein Adsorption Density by Integrated Optical Waveguide Attenuated Total Reflection Spectrometry," *Langmuir* 7:995–999 (1991).

(List continued on next page.)

*Primary Examiner*—Samuel A. Turner
*Attorney, Agent, or Firm*—Klarquist Sparkman Campbell Leigh & Whinston

[57] ABSTRACT

Chemical and biosensors are disclosed. An optical waveguide is used to conduct electromagnetic radiation by total internal reflection in parallel through a reference waveguide portion and at least one analyte waveguide portion. The electromagnetic radiation is then converged into an exit beam. The external surface of at least the analyte portion is covalently modified, or functionalized, relative to the reference portion. Resulting interaction of the functionalized surface with molecules comprising an analyte causes a phase change in the electromagnetic radiation passing through the analyte portion relative to the reference portion sufficient to generate a corresponding and measurable interference pattern in the exit beam. A waveguide surface is functionalized by exposure to a reagent, having molecules each comprising a nitrenogenic group and a functionalizing group, in the presence of energized charged particles such as electrons and ions, photons, or heat, which transform the nitrenogenic reagent to a nitrene intermediate. The resulting reaction causes the functionalizing groups to covalently bond to the surface. The functionalizing groups can then participate in downstream chemistry whereby any of a large variety of functional groups, including biological molecules, can be covalently bonded to the surface. Thus, the waveguide surface can be made selectively responsive to a wide variety of analytes, including cells and other biological structures.

8 Claims, 10 Drawing Sheets

OTHER PUBLICATIONS

Butler et al., "Technique for Enabling Prism Coupling," *Appl. Optics* 29:3879–3882 (1990).

Aboudou et al., "Monolithic Integration of GaAs MSM Photodetector and $SiO_2/Si_3N_4$ Dielectric Optical Waveguide," *Electronics Lett.* 28:52–53 (1992).

Tan et al., "Development of Submicron Chemical Fiber Optic Sensors," *Anal. Chem.* 64:2985–2990 (1992).

Kepley et al., "Selective Surface Acoustic Wave–Based Organophosphonate Chemical Sensor Employing a Self–Assembled Composite Monolayer: A New Paradigm for Sensor Design," *Anal. Chem.* 64:3191–3193 (1992).

Vadgama et al., "Biosensors: Recent Trends A Review," *Analyst* 117:1657–1658, 1663–1667 (1992).

Abbott et al., "Manipulation of the Wettability of Surfaces on the 0.1– to 1–Micrometer Scale Through Micromachining and Molecular Self–Assembly," *Science* 257:1380–1381 (1992).

Stenger et al., "Coplanar Molecular Assemblies of Amino- and Perfluorinated Alkylsilanes: Characterization and Geometric Definition of Mammalian Cell Adhesion and Growth," *J. Am. Chem. Soc.* 114:8435–8442 (1992).

Wring et al., "Chemically Modified, Carbon–Based Electrodes and Their Application as Electrochemical Sensors for the Analysis of Biologically Important Compounds—A Review," *Analyst* 117:1215–1229 (1992).

Yokohama et al., "Synthesis of Poly(ethylene oxide) with Heterobifunctional Reactive Groups at Its Terminals by an Anionic Initiator," *Bioconjugate Chem.* 3:275–276 (1992).

Braybrook et al., "Organic Polymer Surfaces for Use in Medicine: Their Formation, Modification, Characterisation and Application," *Prog. Polym. Sci.* 15:715–734 (1990)

Carlsson et al., "Plasma Modification and Its Effect on Polymer–Polymer and Polymer–Metal Adhesion," *Polymer Materials Science and Engineering* (Fall Meeting 1992, Washington, D.C.) vol. 67, pp. 21–23 (1992).

Cai et al., "Introduction of Functional Groups into Polymer Films via Deep–UV Photolysis or Electron–Beam Lithography: Modification of Polystyrene and Poly(3–octylthiophene) by a Functionalized Perfluorophenyl Azide," *Chem. Mater.* 4:879–884 (1992).

SENSORS EMPLOYING INTERFERENCE OF ELECTROMAGNETIC WAVES PASSING THROUGH WAVEGUIDES HAVING FUNCTIONALIZED SURFACES

ACKNOWLEDGEMENT

This invention was made with U.S. government support under grant number GM 27137 from the National Institute of General Medical Sciences and grant number N00014-92-J-1412 (R&T code 413t011) from the Office of Naval Research. The U.S. government has certain rights in the invention.

CROSS REFERENCE TO RELATED APPLICATION

This application is a continuation-in-part of co-pending U.S. patent application (Ser. No. 006,453) entitled "Chemical Functionalization of Surfaces" naming John F. W. Keana, Martin N. Wybourne, Sui Xiong Cai, and Mingdi Yan as inventors, and filed on Jan. 21, 1993.

FIELD OF THE INVENTION

This invention pertains to chemical sensors and biosensors, in particular such sensors employing an optical waveguide and having response characteristics determined by chemical modifications to a surface of the waveguide.

GENERAL DISCUSSION OF THE BACKGROUND

The present invention is based upon several technologies, namely chemical sensors and biosensors, chemical modification of surfaces, and interferometer technology.

A major goal in sensor technology is toward smaller size and greater sensitivity. Also, increasingly stricter demands of monitoring specificity and selectivity are being imposed, particularly in fields such as environmental monitoring and control, physiological monitoring, diagnostic monitoring, bioprocessing, agriculture, pharmaceuticals, therapeutic monitoring, and even defense and petrochemicals.

A "sensor" is a type of transducer; i.e., a device that responds to an external stimulus or input signal by producing a measurable response having a magnitude bearing a relationship to the magnitude of the external stimulus or input signal.

A "chemical sensor" is a sensor in which a chemical reaction or molecular change in or on the sensor is an important aspect of the production of a measurable response by the sensor.

A "biosensor" is a sensor that incorporates a biological or biomolecular component as a key functional element in the production of a measurable response by the sensor.

Biosensors have been the subjects of great attention due to the high specificity of interactions of many types of biomolecules with molecules of other compounds. See, e.g., Vadgama et al., "Biosensors: Recent Trends, "*Analyst* 117:1657-1670 (1992). However, bridging the gap between knowledge of a particular reaction involving biomolecules and the exploitation of the reaction in a biosensor has often proven to be difficult. For example, in biosensors the biological component is usually in the form of a biolayer that is frequently metastable. Thus, many contemporary biosensors are subject to obfuscating environmental influences. Secondly, biolayers usually need to directly contact the analyte which is frequently present in a complex mixture comprising a large number of other compounds that can interfere with the response of the biolayer to a target analyte or that can be interfacially active and/or possibly detrimental to the biolayer.

An important problem often encountered in making sensors, particularly biosensors, is how to immobilize molecules of the sensing compound (i.e., the "sensing molecules") to a particular situs in or on the sensor such as an appropriate substrate surface. Such immobilization cannot substantially adversely affect the ability of the sensing molecules to respond to significant changes in the measured parameter when the sensing molecules are exposed or otherwise contacted with molecules of an analyte. Such immobilization requires that the sensing molecules retain their reactive specificity toward the corresponding analyte even when the sensing molecules are attached to the situs.

One way to immobilize sensing molecules to a situs is to chemically bond them to the situs. However, particularly with biomolecules, immobilization of sensing molecules by conventional bonding techniques can cause the sensing molecules to change conformation or undergo any of several other changes that can reduce or destroy the capacity of the sensing molecules to respond to the analyte.

Another problem often encountered is that, whereas many substrates such as polymeric substrates have properties that render them desirable for use as substrates, it is often difficult or impossible by contemporary methods to bond sensing molecules to them, particularly using chemistry that does not cause damage to the substrate, the sensing molecules, or both.

Attaching sensing molecules to a substrate can be thought of as a form of chemical modification of, or "functionalization" of, a substrate.

Chemical modification of surfaces has been the subject of intensive research. Examples of such surfaces include polymers, Braybrook et al., *Prog. Polym. Sci.* 15:715–734 (1990); metals, Stratmann, *Adv. Mater.* 2:191– 195 (1990); silica, Bhatia et al., *J. Am. Chem. Soc.* 114:4432–4433 (1992); and graphite, Delamar, *J. Am. Chem. Soc.* 114:5883–5884 (1992). This research has been principally directed toward the development of novel composites, Baum et al., *Chem. Mater.* 3:714–720 (1991); resist materials, MacDonald et al., *Chem. Mater.* 3:435–442 (1991); biosensors, Pantano et al., *J. Am. Chem. Soc.* 113:1832–1833 (1991); and biomaterials, Allcock et al., *Chem. Mater.* 3:450–454 (1991). Recently, surface modification has been combined with photolithography to spatially direct the synthesis of peptides or oligonucleotides, Fodor et al., *Science* 251:767–773 (1991) and Kiederowski, *Angew. Chem. Int. Ed. Eng.* 30:822–823 (1991); and immobilization of biopolymers. Rozsnyai et al., *Angew. Chem. Int. Ed. Eng.* 31:759–761 (1992). Most of the surface modification processes known in the art involve sequential treatment of surfaces with chemical reagents. Id. Only a few such studies have involved the use of azides as surface-modification reagents. Breslow, in Scriven (ed.) *Azides and Nitrenes*, chapter 10, Academic Press, NY (1984); Harmer, *Langmuir* 7:2010–2012 (1991).

Examples of existing methods for modifying polymer films include sulfonation of polystyrene, Gibson et al., *Macromolecules* 13:34 (1980); sulfonation of poly(aryloxy-)phosphazenes, Allcock et al., *Chem. Mater.* 3:1120 (1991); plasma treatment of polyester, Porta et al., *Chem. Mater.* 3:293 (1991); base hydrolysis of polyimide, Lee et al.,

*Macromolecules* 23:2097 (1990); base hydrolysis of polyphosphazenes, Allcock et al., *Chem. Mater.* 3:1441 (1991); and base treatment of poly(vinylidene fluoride), Dias et al., *Macromolecules* 17:2529 (1984).

Another conventional method for modifying polymers comprises exposing the surface of a hydrocarbon polymer such as polyethylene with nitrene or carbene intermediates generated in the gas phase. Breslow, in Scriven (ed.), *Azides and Nitrenes,* chapter 10, Academic Press, NY (1984). Also, difluorocarbene generated in solution has been reported to modify 1,4-polybutadienes. Siddiqui et al., *Macromolecules* 19:595 (1986).

Perfluorophenyl azides (PFPAs) have been shown to exhibit improved CH-insertion efficiency over their non-fluorinated analogues when the PFPAs were photolyzed in hydrocarbon solvents such as cyclohexane or toluene. Keana et al., *Fluorine Chem.* 43:151 (1989); Keana et al., *J. Org. Chem.* 55:3640 (1990); Leyva et al., *J. Org. Chem.* 54:5938 (1989); and Soundararajan et al., *J. Org. Chem.* 55:2034 (1990). PFPAs were initially developed as efficient photo-labeling reagents. Cai et al., *Bioconjugate Chem.* 2:38 (1991); Pinney et al., *J. Org. Chem.* 56:3125 (1991); and Crocker et al., *Bioconjugate Chem.* 1:419 (1990). Recently, bis-(PFPA)s have been shown to be efficient cross-linking agents for polystyrene, Cai et al., *Chem. Mater.* 2:631 (1990); and poly(3-octylthiophene), Cai et al., *J. Molec. Electron.* 2:63 (1991).

Chemical sensors and biosensors are known that exploit certain aspects of surface modification technology. For example, as disclosed in Kepley et al., *Anal. Chem.* 64:3191–3193 (1992), a mass-sensitive surface-acoustic wave (SAW) substrate is chemically modified by a monolayer of carboxylate-terminated n-alkanethiol molecules terminated by $Cu^{+2}$ ions bound to the carboxylate termini. Such a sensor responds reversibly to the nerve-agent simulant diisopropyl methylphosphonate by binding molecules of the simulant to the terminal $Cu^{2+}$ ions. Such binding causes a perturbation in the SAW that is proportional to the mass of simulant bound to the terminal $Cu^{+2}$ ions.

Chemical and biosensors have also been made that respond to changes in light passing through waveguides. One example of such a sensor is disclosed in Norris, *Analyst* 114:1359 (1989), wherein the total internal reflectance experienced by light during transmission through an optical waveguide is exploited. Total internal reflection permits the surface of the waveguide to be effectively "interrogated" by the light passing through the waveguide.

In another example, Tan et al., *Anal. Chem.* 64:2985–2990 (1992), optical fibers are drawn into submicron optical fiber tips that are chemically modified for use as pH probes. Chemical modification of the tips is performed by incorporating fluoresceinamine into an acrylamide-methylene-bis(acrylamide) copolymer and covalently attaching the copolymer to silanized fiber tips by photoinitiated polymerization.

SUMMARY OF THE INVENTION

The present invention provides sensor elements and sensors that exploit total internal reflection of electromagnetic radiation in a waveguide. According to one aspect of the present invention, the waveguide shares certain characteristics with a "Mach-Zehnder" interferometer as known in the art. I.e., the waveguide has at least two separate portions. Electromagnetic radiation is passed in parallel down the waveguide portions, then converged into an "exit beam." The waveguide is fabricated of a material exhibiting a refractive index for the electromagnetic radiation.

According to another aspect of the present invention, one of the waveguide portions through which the electromagnetic radiation passes in parallel serves as a "reference" portion and another of said portions of the waveguide serves as an "analyte" portion.

According to yet another aspect of the present invention, the analyte portion has an external surface that is chemically modified, or "functionalized," so as to interact with molecules comprising an analyte. The interaction of the functionalized surface with the analyte, such as binding of the analyte to the functionalized surface, is sufficient to impart a phase change to the electromagnetic radiation passing through the analyte portion relative to the electromagnetic radiation passing through the reference portion. The phase change is sufficient to generate a corresponding interference pattern in the exit beam. The interference pattern in the exit beam renders the exit beam detectably different from an exit beam that is produced when no analyte is present on the surface of the analyte portion.

According to another aspect of the present invention, the reference and analyte portions of the waveguide each have first and second ends, wherein the first ends are coupled to an incoming waveguide portion and the second ends are coupled to an outgoing waveguide portion. The incoming portion serves to introduce the electromagnetic radiation into the first ends. The outgoing portion serves to converge the electromagnetic radiation exiting the second ends.

According to yet another aspect of the present invention, the waveguide can be very small. For example, for single-mode transmission of wavelengths of electromagnetic radiation in or near the visible portion of the electromagnetic spectrum, the transverse dimensions of the waveguide can be on the order of micrometers. Thus, the resulting sensors can be placed virtually anywhere for sensing purposes, including in the presence of living cells, and have extremely rapid response times. In addition, they exhibit exquisite sensitivity to very small amounts of the analyte.

According to another aspect of the present invention, such small waveguides can be fabricated on the surface of a rigid base material having a refractive index lower than the refractive index of the waveguide. If necessary, an intermediate material having a sufficiently low refractive index can be applied first to a surface of the base material having refractive index that is too high relative to the refractive index of the waveguide.

Sensors according to the present invention can comprise biosensors. To fabricate such a biosensor, the analyte portion of the waveguide is functionalized by attaching molecules of a biological substance such as a protein or antibody. Such sensors are responsive (depending upon exactly what functional groups are attached to the surface of the analyte portion) to analytes that can comprise biological structures such as viruses and other microorganisms, cells, cell organelles, membrane components, and a wide range of biological molecules.

The waveguide can be any non-fluid substance that exhibits a refractive index to the electromagnetic radiation to be passed through the waveguide. For example, waveguide substances can include, but are not limited to, a wide variety of polymeric materials and siliceous materials. The waveguide material can also be a semiconductor material such as silicon, silicon oxide, gallium arsenide, and other semiconducting materials (doped or not doped).

According to yet another aspect of the present invention, waveguide surfaces are functionalized by exposing the surface to a nitrenogenic functionalizing reagent in the presence of a reaction-energy source such as photons, electrons, or heat. In the presence of the reaction-energy source, the functionalizing reagent forms a nitrene intermediate that covalently reacts with —CH, —NH, —OH, —C=C—, —C—C— and other groups on the waveguide surface so as to cause "nitrene addition" or "nitrene insertion" of the functionalizing reagent to the surface.

In order to form nitrene intermediates, the functionalizing reagent must terminate with an azide group or analogous chemical group capable of forming a reactive nitrene when exposed to a reaction-energy source.

The waveguide surface can be functionalized via either a single-stage or a multi-stage process. In a multi-stage process, each stage typically involves different functionalizing reagents. In both single- and multi-stage processes, at least one stage involves a nitrenogenic functionalizing reagent.

In a single-stage process, each molecule of the functionalizing agent comprises, in addition to the nitrenogenic group, a functionalizing group covalently coupled to the nitrenogenic group. The functionalizing group can be virtually any desired chemical group that does not cross-react with the nitrene intermediate or otherwise significantly interfere with the nitrene addition reaction of the functionalizing agent with the substrate surface. E.g., the functionalizing group can be selected from, but is not necessarily limited to, radioactive labels, fluorescent labels, enzymes, pharmacologically active groups, diagnostically active groups, antibodies, nucleic acids, surfactants, and any of a wide variety of other groups.

Functionalizing reagents adapted to functionalize the waveguide surface in multi-stage reactions can be configured in several ways. According to one method, a first functionalizing reagent is reacted with the waveguide surface so as to achieve covalent attachment of the first functionalizing-reagent molecules to the waveguide surface; afterward, a second functionalizing reagent is added so as to react with, and therefore covalently bond to, the attached first functionalizing-reagent molecules. In such a method, the first functionalizing reagent comprises molecules each comprising, in addition to the nitrenogenic group, a first functionalizing group adapted to participate in downstream chemistry after the first functionalizing reagent has been covalently bonded to the substrate surface via nitrene addition. For example, the first functionalizing group can be an active ester that is reactive with -NH groups, —OH groups, or other nucleophilic groups on molecules of a second functionalizing reagent. The second functionalizing reagent, then, can provide a second functionalizing group ultimately desired to be attached to the waveguide surface, such as an enzyme, antibody, diagnostic agent, or therapeutic agent.

An alternative multi-stage process comprises first reacting the second functionalizing reagent (comprising the second, or ultimately desired, functionalizing group) with the first functionalizing reagent (including a nitrenogenic group); then, in a second reaction, reacting the product of the first reaction with the waveguide surface in the presence of a reaction-energy source so as to covalently attach the product of the first reaction to the waveguide surface via nitrene addition.

A class of preferred functionalizing reagents for single- and multi-stage processes according to the present invention consists of N-hydroxysuccinimide active ester-functionalized perfluorophenyl azides (NHS-PFPAs). The NHS active ester groups become covalently attached to the waveguide surface via generation during the reaction of highly reactive nitrene intermediates derived from the PFPA portion of the reagent molecules. (The reactive nitrene portion of the intermediates are preferably constrained structurally such that the nitrene portion cannot react intramolecularly with the NHS active ester portion.) Thus, the waveguide surface becomes "modified" (i.e., "functionalized"). Afterward, the active esters can participate in further reactions with a variety of reagents containing primary amines or hydroxyls (such as biomolecules) by way of amide or ester formation, respectively.

DETAILED DESCRIPTION

1. General Sensor Configuration

According to the present invention, chemical sensors and biosensors are provided that are configured as interferometers. The preferable configuration is a modified Mach-Zehnder interferometer having a reference branch and at least one branch (termed herein the "analyte branch") adapted to interact with an analyte.

An interferometer is an instrument that, in general, splits a beam of electromagnetic radiation into two or more beams which are routed along separate paths and then recombined. A change in one of the split beams relative to another of the split beams can result in generation of an interference pattern in the recombined beam. Interferometers have been employed for measuring film thicknesses (e.g., "Fizeau interference"), surface microtopography, performance of optical elements (e.g., "Twyman-Green interferometry"), and gas density. In addition, optical interference has been exploited to perform spectroscopy (e.g., "Czerny-Turner monochromator", "Fabry-Perot spectroscopy").

In a conventional Mach-Zehnder interferometer, a first beam splitter is used to generate at least two divergent beams from a single source beam of electromagnetic radiation. Each branch beam is reflected so as to cause the divergent beams to converge. The convergent beams are recombined using a second beam splitter. The Mach-Zehnder interferometer is typically used for measuring gas flow around obstacles in wind tunnels and the like. This is possible because the index of refraction of a gas is proportional in many cases to the gas density. A test chamber is placed to allow one branch beam to pass through it, with another branch beam serving as a reference beam. A pattern of interference fringes results from the reunion of the branch beams. When gas density changes as a result of localized compression, the optical path length of the first branch beam is changed and the interference pattern is correspondingly modified.

A laboratory version of a Mach-Zehnder interferometer typically routes the light beams through a gas (such as air) and relies upon mirrors and conventional beam splitters. According to the present invention, the entire interferometer is preferably fabricated as a single optical waveguide unit from a material exhibiting a refractive index to an appropriate type of electromagnetic radiation that will pass through the waveguide.

As used herein, the term "light" shall be understood to mean electromagnetic radiation in general having a wavelength (or range of wavelengths) suitable for the analyte of interest and for the material from which the interferometer is made. The electromagnetic radiation can be visible light but can also be other wavelengths such as, but not limited to, infrared and ultraviolet light. Preferably, the wavelength of light used with an interferometer according to the present invention is within the range of about 0.3 to about 2.0 μm. The electromagnetic radiation can be non-polarized or polarized.

Figure 1:
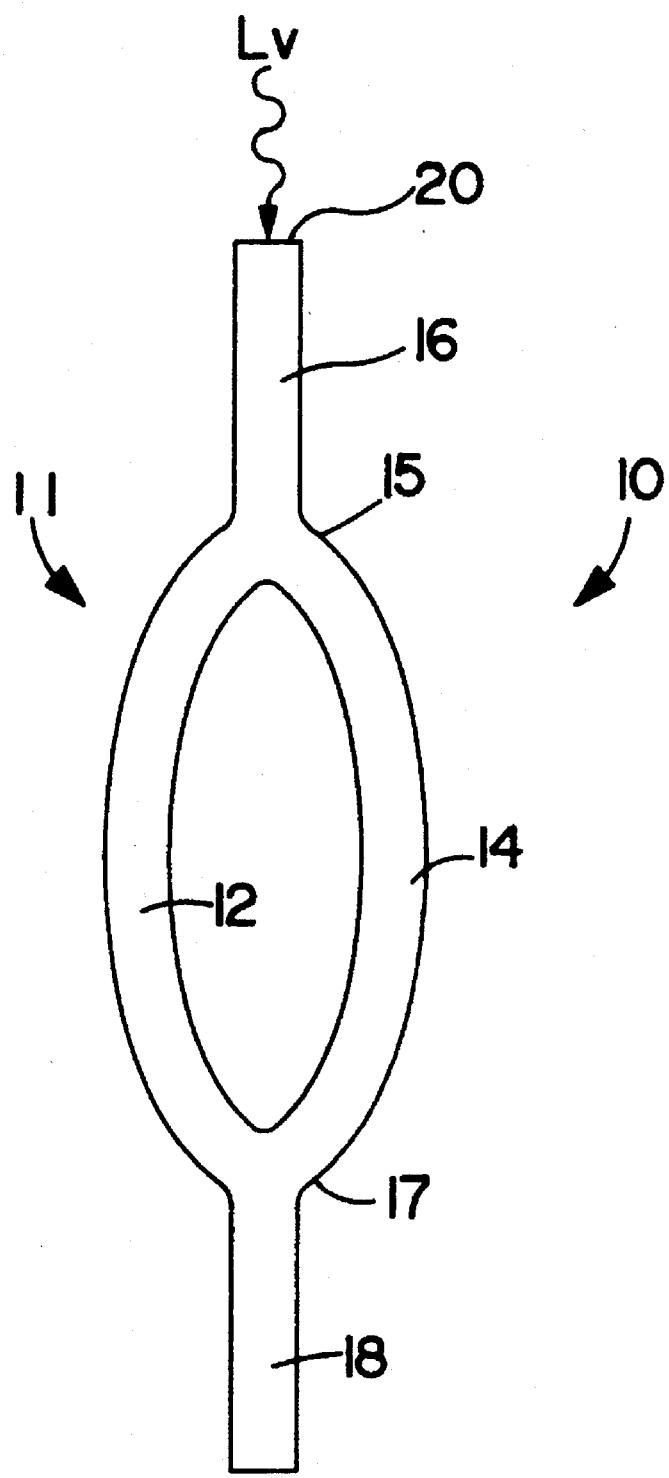
FIG. 1 is a schematic diagram of an embodiment of an interferometer according to the present invention.

A representative interferometer 10 according to the present invention is shown in FIG. 1. The interferometer 10 is constructed of a single optical waveguide 11 having a reference branch 12 and an analyte branch 14. The reference branch 12 and the analyte branch 14 are joined at a first junction 15 to a incoming waveguide 16 and at a second junction 17 to an outgoing waveguide 18. Light (hv) enters the incoming waveguide 16 at or near its terminus 20 and propagates as a beam down the length of the incoming waveguide 16 toward the first junction 15. At the first junction 15, the waveguide splits the light beam so as to pass a portion of the light beam into the reference branch 12 and a portion into the analyte branch 14. After passing through the reference and analyte branches, the light beams are reunited at the second junction 17 and enter the outgoing waveguide 18. Any relative phase change in the light passing through the analyte branch 14 relative to the light passing through the reference branch 12 will generate interference in the outgoing waveguide 18 that will be detected as a change in the transmitted intensity of the light.

The interferometer is made sensitive to an analyte of interest by chemically functionalizing the surface of the analyte branch using functionalization chemistry as described in detail below. The reference branch is left either not functionalized or functionalized differently from the analyte branch, thereby allowing the interferometer to "compare" light passing through the analyte branch with light passing through the reference branch. Functionalization renders the surface of the analyte branch capable of binding analyte molecules or otherwise renders the analyte branch responsive to analyte molecules in a way that alters the surface chemistry of the analyte branch. As described at length below, various functional groups can be bonded to the analyte arm, thereby permitting the covalent attachment of a very wide variety of analyte-responsive molecules or chemical groups. For example, biological molecules can be attached to the analyte branch such as (but not limited to): enzymes, antibodies, nucleic acids, enzyme substrates, and cell-surface antigens.

The analyte branch can be functionalized to be sensitive not only to specific analyte molecules, but also to such entities as intact viable cells and other biological structures that can also serve as analytes. Thus, it is possible using a sensor according to the present invention to assay tissue for the presence of certain cells that bind to cell-specific antibodies or antigens bonded to the analyte branch. Likewise, the present invention makes it possible to assay a material for the presence of viruses that bind to virion-specific biomolecules bonded to the analyte branch of the waveguide.

As discussed briefly above, an interferometer according to the present invention transmits light through the optical waveguide. Some of the light passing through the interferometer passes through the reference branch and some passes through the analyte branch which has a functionalized surface. The light experiences total internal reflectance as it passes through the optical waveguide. According to the principles of total internal reflection as currently understood, the electrical vectors of the optical standing waves created at the longitudinal walls of the waveguide as the beam reflects therefrom extend into the medium surrounding the waveguide. If analyte molecules attach to the functionalized surface of the analyte-branch waveguide (or otherwise cause a chemical change to the functionalized surface), the beam passing through the analyte branch is altered in a manner distinctive for the analyte and the way the analyte interacts with the functionalized surface. The light beam passing through the reference-branch waveguide is not similarly altered. Therefore, when the analyte-branch and reference-branch light beams are reunited upon entering the outgoing waveguide, a distinctive interference pattern is created. This generation of, or change in, the interference pattern is readily detectable by conventional methods.

The interferometer can have either one or multiple analyte branches. In the latter instance, an interferometer can be made responsive to more than one analyte or more sensitive to a particular analyte. Each analyte branch can be similarly or differently functionalized.

The lowest practical size of the interferometer will be determined by the absorption of the electromagnetic radiation propagating through the waveguide. Single-mode operation will occur for electromagnetic radiation of wavelength below the cutoff wavelength of the waveguide. Electromagnetic radiation of wavelength above the cutoff wavelength of the waveguide will cause multimode operation. The cutoff wavelength of a waveguide is well known to persons skilled in the waveguide art.

Waveguides having very small transverse dimensions (e.g., in microns) are preferably formed upon, or otherwise supported by, a rigid base. Materials directly contacting the interferometer waveguide, such as a base material, should have a refractive index that is lower than the refractive index of the waveguide. The greater the difference in refractive index of the base material (or other material contacting the waveguide) relative to the waveguide material, the better.

Representative base materials, not intended to be limiting, include silicon dioxide (n=1.41 to 1.49); fused silica (n=1.4); quartz (n=1.55); glass (n=1.5 to 1.9, depending on the specific type); as well as gallium arsenide, silicon, and other semiconducting materials.

In instances wherein the interferometer is supported by a base material, the waveguide can be fabricated directly on the base material. When an especially desirable base material has a refractive index that is too high relative to the waveguide material, the base material can be first coated with an intermediate material having a lower refractive index, then the waveguide is formed on the surface of the intermediate material.

Many suitable base materials (including many synthetic polymers and inorganic materials such as silicon dioxide and quartz) have refractive indices that are insufficiently different from many suitable waveguide materials. Therefore, it is frequently necessary or at least desirable to interpose an intermediate material having a lower refractive index than the base material between the base material and the waveguide.

The waveguide is fabricated of a material exhibiting a refractive index (designated by the variable "n") to the electromagnetic radiation that will pass through the waveguide. The refractive index of the waveguide material should be greater than the refractive index of the base material and of any other substance (such as air or liquids containing the analyte) contacting the waveguide.

The waveguide material is preferably a synthetic polymer selected from a wide variety of available synthetic polymers. A partial list of candidate polymers is included in Table I, along with corresponding refractive index values (measured at 20°–25° C.).

TABLE I

| Polymer | n |
| --- | --- |
| Poly(tetrafluoroethylene) | 1.35–1.38 |
| Poly(vinylidine fluoride) | 1.42 |
| Poly(oxypropylene) | 1.4495 |
| Poly (vinyl isobutyl ether) | 1.4507 |
| Poly(vinyl ethyl ether) | 1.4540 |
| Poly(oxyethylene) | 1.4563 |
| Poly(vinyl butyl ether) | 1.4563 |
| Poly(vinyl pentyl ether) | 1.4581 |
| Poly(vinyl hexyl ether) | 1.4591 |
| Cellulose acetate butyrate | 1.46–1.49 |
| Poly(vinyl octyl ether) | 1.4613 |
| Poly(vinyl decyl ether) | 1.4628 |
| Poly(butyl acrylate) | 1.4631 |
| Poly(vinyl docecyl ether) | 1.4640 |
| Poly(vinyl propionate) | 1.4665 |
| Poly(vinyl acetate) | 1.4665 |
| Poly(vinyl methyl ether) | 1.467 |
| Poly(ethyl acrylate) | 1.4685 |
| Cellulose propionate | 1.47–1.49 |
| Cellulose acetate propionate | 1.47 |
| Benzyl cellulose | 1.47–1.58 |
| Phenol-formaldehyde | 1.47–1.70 |
| Cellulose triacetate | 1.47–1.48 |
| Poly(vinyl methyl ether) | 1.4700 |
| Poly(methyl acrylate) | 1.472–1.480 |
| Poly(propylene) ($\eta$ = .9575 g/cm$^3$) | 1.4735 |
| Poly(ethylene-co-propylene) | 1.4748–1.48 |
| Poly(vinyl formate) | 1.4757 |
| Ethyl cellulose | 1.479 |
| Poly(vinyl acetal) | 1.48–1.50 |

TABLE I-continued

| Polymer | n |
| --- | --- |
| Cellulose acetate | 1.48–1.50 |
| Poly(oxymethylene) | 1.48 |
| Poly(vinyl butyral) | 1.48–1.49 |
| Poly(ethyl methacrylate) | 1.485 |
| Poly(methyl methacrylate) | 1.4889 |
| Poly(vinyl alcohol) | 1.9–1.53 |
| Methyl cellulose | 1.497 |
| Poly(urethanes) | 1.5–1.6 |
| Poly(1,2-butadiene) | 1.5000 |
| Poly(vinyl formal) | 1.50 |
| Cellulose nitrate | 1.5–1.514 |
| Poly(propylene) ($\eta$ = .9075 g/cm$^3$) | 1.5030 |
| Poly(isobutene) | 1.5505–1.51 |
| Poly(ethylene) ionomer | 1.51 |
| Poly(oxyethylene) (HMW) | 1.51–1.54 |
| Poly(ethylene) ($\eta$ = .914 g/cm$^3$) | 1.51 |
| Poly(ethylene) ($\eta$ = .94–945 g/cm$^3$) | 1.52–1.53 |
| Poly(ethylene) ($\eta$ = .965 g/cm$^3$) | 1.545 |
| Poly(butene) (isotactic) | 1.5125 |
| Poly(vinyl methacrylate) | 1.5129 |
| Poly(1,3-butadiene) | 1.5154 |
| Poly(acrylonitrile) | 1.52 |
| Poly(isoprene) | 1.521 |
| Poly(ester) resin-50% styrene | 1.523–1.54 |
| Poly(acrylic acid) | 1.5270 |
| Poly(acrolein) | 1.529 |
| Poly(1-vinyl-2-pyrrolidone) | 1.53 |
| "Nylon 6" | 1.53 |
| "Nylon 6.6" | 1.53 |
| Poly(butadiene-co-styrene) | 1.53 |
| Cellulose | 1.54 |
| Poly(vinyl chloride) | 1.54–1.55 |
| Urea-formaldehyde resin | 1.54–1.56 |
| Poly(abietic acid) | 1.546 |
| Poly(vinylfuran) | 1.55 |
| Epoxy resins | 1.55–1.60 |
| Poly(benzyl methacrylate) | 1.5680 |
| Poly(phenyl methacrylate) | 1.5705 |
| Poly(vinyl benzoate) | 1.5775 |
| Poly(o-methylstyrene) | 1.5874 |
| Poly(styrene) | 1.59–1.592 |
| Poly(vinylidene chloride) | 1.60–1.63 |
| Poly(sulfides) | 1.6–1.7 |
| Poly(sulfone) | 1.633 |
| Poly(2-vinylthiophene) | 1.6376 |
| Urea-thiourea-formaldehyde resin | 1.660 |
| Poly(vinylnaphthalene) | 1.6818 |
| Poly(vinylcarbazole) | 1.683 |
| Napthalene-formaldehyde resin | 1.696 |
| Phenol-formaldehyde resin | 1.70 |

As stated above, the foregoing list is not exhaustive. Other candidate waveguide polymers include poly(imides) and poly(3-octylthiophene).

Examples of other materials that can be used to make waveguides include (but are not limited to): silicon oxide, silicon nitride, gallium arsenide, as well as glass and other siliceous materials. As is understood by persons skilled in the art, the "transparency" of the waveguide material to electromagnetic radiation depends upon the wavelength of the electromagnetic radiation intended to pass through the waveguide.

When forming the waveguide from a synthetic polymer, the polymer molecules can become oriented. Molecular orientation can affect the refractive index of the waveguide because the refractive index of a polymer can change substantially from one axis to another for an oriented polymer. Thus, polymers having an average refractive index that is too low may be more suitable when the molecules thereof have a specific orientation relative to the waveguide.

Suitable polymers include not only pure polymers but also polymer blends. See, Paul et al., *Multicomponent Polymer Mixtures*, ACS Symposium Series #211 (1986). The polymers need not be insoluble in aqueous liquids. A representative example is poly(2-ethyl-2-oxazoline) having an index of refraction of 1.52, Chiu et al., in Glass (ed.), *Water-soluble Polymers, Beauty with Performance*, ACS Symposium Series #213, pp. 425–433 (1986).

To achieve improved performance of the interferometer, it is preferred that the reference branch (if non-functionalized) and the incoming and outgoing waveguides be clad with an inert material having a low refractive index (relative to the waveguide). Preferred cladding materials include, but are not limited to, epoxy resins and poly(methyl methacrylate). Cladding helps prevent surface contamination which could cause undesired phase changes.

Other physical characteristics of the waveguide can also affect the performance of the waveguide. For example, it is important that the waveguide not have excessive edge roughness. In addition, referring further to FIG. 1, the radius of curvature of the reference branch 12 and analyte branch 14 should be as large as practicable; the larger the radius, the better. The radius can be adjusted as necessary during the fabrication process.

Waveguides can also be formed on the base material using technology adapted for forming polymer integrated optical waveguides. See, e.g., Saavedra et al., *Appl. Spectroscopy* 44:1210 (1990); Saavedra et al., *Langmuir* 7:995–999 (1991).

With waveguides having transverse dimensions, for example, in micrometers, electromagnetic radiation of a suitable wavelength can be introduced into the waveguide using prism coupling or grating coupling as known in the art. See, e.g., Butler et al., *Appl. Optics* 29:3879–3880 (1990).

Interference in light waves passing through the outgoing waveguide can be detected by fringe counting (under conditions of large phase changes) or by measuring the changes in the transmitted light intensity through the outgoing waveguide.

Several sensors can be employed simultaneously to achieve differential detection of analytes. In addition, a given sensor can have multiple analyte branches each differently functionalized, allowing the sensor to be used as a spectroscopic sensor.

Sensors according to the present invention have extremely rapid response times, particular sensors having transverse dimensions on the order of microns.

2. General Functionalization Technology

For most applications of sensors according to the present invention, only the analyte branch(es) of a sensor is functionalized. However, since an interferometer according to the present invention effectively detects a differential transmission of light through the analyte branch(es) relative to the reference branch, it is possible to also functionalize the reference branch, but in a different way from the analyte branch.

The following terms are used herein:

A "substrate" is a non-fluid material providing a surface that can be functionalized according to the present invention, the substrate is the analyte branch(es) (and possibly also the reference branch) of an interferometer as discussed above. With respect to the functionalization technology described below, the substrate can comprise molecules (e.g., thermoplastic polymer molecules), a thermoset molecular network (e.g., cross-linked polymer molecules), or other atomic or molecular association such as found in certain glasses and crystals.

A "surface molecule" is a substrate molecule having at least a portion thereof present on the substrate surface.

A "polymeric substrate" is a substrate comprising polymer molecules or a network of polymer molecules.

A "polymer molecule" is a large molecule formed by the covalent linking together of smaller molecules termed "monomers." The monomers present in a polymer molecule can be the same or different. Polymer molecules can be natural, such as (but not limited to) cellulose, starch, proteins, and nucleic acids; or synthetic such as (but not limited to) nylon and polyethylene. In a substrate, polymer molecules can be associated with each other in any of several ways, including non-covalently (as a thermoplastic) or a covalently cross-linked network (as a thermoset).

A "functionalized substrate" is a substrate to which one or more functional groups are covalently bonded according to the present invention.

A "functional group" is a group of one or more atoms bonded together in an organized way so as to have a desired chemical property. According to the present invention, a functional group can, when covalently bonded to a substrate surface according to the present invention, participate in one or more additional bonding reactions with either a similar functional group or a different type of functional group. Such bonding reactions can result in: (a) attachment to the functional groups of any of a variety of additional functional groups; or (b) coupling together (cross-linking) of the functionalized substrate molecules.

The term "functionalized polymer" can pertain to either a functionalized polymeric substrate or a functionalized polymer molecule.

A "functionalizing reagent" according to the present invention is a reagent adapted for functionalizing a substrate according to the present invention. Molecules of functionalizing agents have at least one nitrenogenic group (as a first functional group) coupled to a second functional group, wherein the nitrenogenic group is preferably constrained by the functionalizing-reagent molecular structure between the nitrenogenic group and the functional group The nitrenogenic groups are capable under reaction conditions of functionalizing a substrate surface.

A "nitrenogenic group" on a functionalizing reagent is a chemical moiety that, when exposed to a reaction-energy source, becomes a nitrene group.

A "nitrene group" (also generally termed "nitrene" or "nitrene intermediate") is a particular form of nitrogen group that can be depicted as a singlet by the structure: R—$\underline{\text{N}}$, and as a triplet by the structure: R—$\underline{\dot{\text{N}}}$. Nitrenes are regarded by persons skilled in the art as the nitrogen analogs of carbenes. Like carbenes, nitrenes are generally regarded as intermediates. Nitrenes are highly reactive and generally cannot be isolated under ordinary conditions. However, certain chemical reactions such as reactions according to the present invention would not otherwise be explainable by known reaction mechanisms without the presumed existence of nitrenes. Important nitrene reactions can be summarized by the following:

(a) Nitrenes, including aryl nitrenes, can undergo addition reactions at —CH sites and at —NH sites; e.g.:

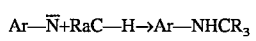

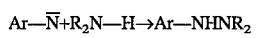

(b) Nitrenes can also undergo addition at —C—C— and —C=C— bonds; e.g.:

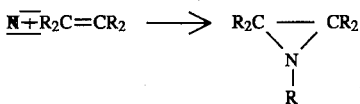

As used herein, the term "addition reaction" when used in the context of reactions of the nitrene group of the functionalizing reagent with surface molecules, generally refers to any of the various addition and insertion reactions that nitrenes can undergo with molecules on the substrate surface according to the present invention.

According to the present invention, a functionalizing reaction occurs when a functionalizing reagent comprising a nitrenogenic group is exposed to a reaction-energy source, which converts the nitrenogenic group to a nitrene intermediate. The functionalizing reaction proceeds by reaction of the nitrene intermediate with the substrate surface.

A "reaction-energy source" is an energy source that drives a functionalizing reaction according to the present invention by, in particular, converting nitrenogenic groups on functionalizing reagent molecules to nitrenes which react with the substrate surface. Suitable reaction-energy sources include (but are not limited to): photons (such as ultraviolet (UV) light, deep-UV light, laser light, X-rays, and heat in the form of infrared radiation or conductive heating), energized electrons (such as an electron beam), and energized ions (such as an ion beam). These reaction-energy sources are conventionally used for such tasks as lithography, scanning microscopy, and, in the case of UV and visible photons, effecting photochemical reactions and excitation of fluorescent molecules.

A "functionalizing reaction" is a reaction in which a substrate surface is functionalized according to the present invention. A functionalizing reaction can consist of one or more stages. At least one stage involves the reaction in the presence of a reaction-energy source of the substrate surface with molecules of a functionalizing reagent comprising nitrenogenic groups.

According to the present invention, a substrate surface is functionalized by a chemistry whereby functional groups on functionalizing reagent molecules become covalently bonded to the surface. Such covalent bonding is achieved by conversion of nitrenogenic groups on the functionalizing reagent molecules (the functionalizing reagent molecules also each comprising a desired functional group as set forth below) to a nitrene intermediate highly reactive with the substrate surface by exposure of the functionalizing reagent molecules to a reaction-energy source.

The functionalizing reagent is preferably selected from a group consisting generally of: aryl azides, alkyl azides, alkenyl azides, alkynyl azides, acyl azides, and azidoacetyl derivatives, all capable of carrying a variety of substituents. Most preferably, fluorine (and/or chlorine) atoms are present to the maximum extent possible in the positions on the functionalizing reagent molecule adjacent the azide group.

Each of the foregoing azides may also contain within the same molecule any of the following functional groups, constrained structurally from reacting with the nitrene moiety after the nitrene moiety is generated:

(a) carboxyl groups and various derivatives thereof such as (but not necessarily limited to): N-hydroxysuccinimide esters; N-hydroxybenztriazole esters; acid halides corresponding to the carboxyl group; acyl imidazoles; thioesters; p-nitrophenyl esters; alkyl, alkenyl, alkynyl and aromatic esters, including esters of biologically active (and optically active) alcohols such as cholesterol and glucose; various amide derivatives such as amides derived from ammonia, primary, and secondary amines and including biologically active (and optically active) amines such as epinephrine, dopa, enzymes, antibodies, and fluorescent molecules;

(b) alcohol groups, either free or esterified to a suitable carboxylic acid which could be, for example, a fatty acid, asteroid acid, or a drug such as naprosin or aspirin;

(c) haloalkyl groups wherein the halide can be later displaced with a nucleophilic group such as a carboxylate anion, thiol anion, carbanion, or alkoxide ion, thereby resulting in the covalent attachment of a new group at the site of the halogen atom;

(d) maleimido groups or other dienophilic groups such that the group may serve as a dienophile in a Dieis-Alder cycloaddition reaction with a 1,3-diene-containing molecule such as, for example, an ergosterol;

(e) aldehyde or ketone groups such that subsequent derivatization is possible via formation of well-known carbonyl derivatives such as hydrazones, semicarbazones, or oximes, or via such mechanisms as Grignard addition or alkyllithium addition; and (f) sulfonyl halide groups for subsequent reactions with amines, for example, to form sulfonamides.

A general reaction by which a functionalizing reagent is converted to a nitrene intermediate is:

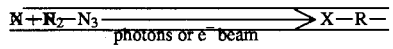

where X is the functional group and R is an aromatic ring, heteroaromatic ring, or other carbon-containing fragment.

A reaction-energy source comprising UV light can be supplied to the reaction by, for example, one of the following representative procedures: (a) The sample is placed in a well of a Rayonet Photochemical Reactor fitted with either 350-nm, 300-nm, or 254-nm lamps and irradiated at ambient temperature for several minutes under air. The duration of the irradiation can be adjusted to change the exposure dose. (b) The sample is irradiated through a high-resolution photomask, for example, by (but not limited to) projection UV lithography. (c) Photolysis is carried out in a KSM Karl Suss deep-UV contact aligner using a contact high-resolution photomask. It will be readily appreciated by persons skilled in the art that such procedures can also be generally used to provide the functionalizing reaction with photons of wavelengths other than UV.

A reaction-energy source comprising electrons can be supplied to the reaction by the following representative procedure: The sample is irradiated under vacuum by an electron or particule beam with an energy selected within the range 1–40 kV. (A representative electron-beam source is a JEOL 840A electron microscope modified for electron-beam lithography.) The beam is stepped across the surface of the treated substrate to expose certain areas and not others. A dwell time at each step can be adjusted to change the exposure dose.

Particularly effective functionalizing reagents are selected from the group of perfluorophenyl azides (PFPAs) derived from 4-azido-2,3,5,6-tetrafluorobenzoic acid in which the carbonyl group is further activated through reactive ester, amide, acid halide, or mixed anhydride formation.

For example, and not intended to be limiting, representative functionalized perfluorophenyl azides have the general structure:

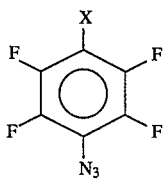

wherein X can be any of the following: CN, CONH$_2$, CHO, CO$_2$Me, COMe, NO$_2$, CO$_2$H, COCl, CO-Imidazole, CONHS, CH$_2$OH, CH$_2$NH$_2$, COCH$_2$Br, N-maleimido, NH-biotinyl, CONH—R (where R is a polypeptide moiety), CONH—X—S—S—Y—NH-biotinyl (where X and Y are spacer atoms and the S—S bond is reductively cleavable at a later stage), and CONHS—SO$_3$Na.

Representative activated PFPAs include (but are not limited to) the N-hydroxysuccinimide (NHS) ester A (also designated "NHS-PFPA"), the p-nitrophenyl ester B, the 1-hydroxybenzotriazole ester C, the acyl imidazole D, the acid chloride E, the mixed anhydride F and the 2,2,2-trichloroethyl ester G:

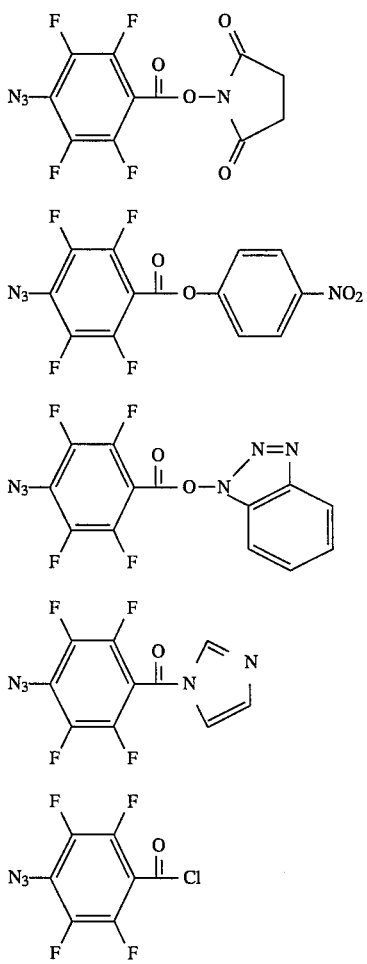

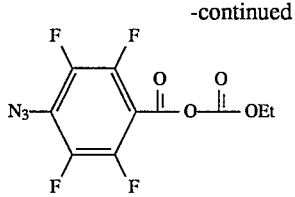

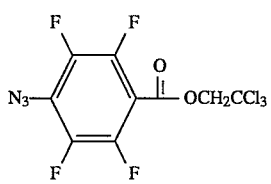

In addition to the foregoing candidate functionalizing reagents, it is possible to utilize other PFPAs having "spacers" situated between the reactive functional group and the PFPA moiety, such as:

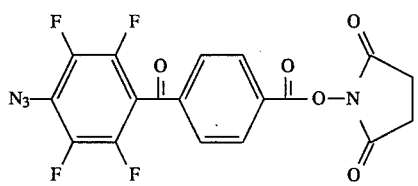

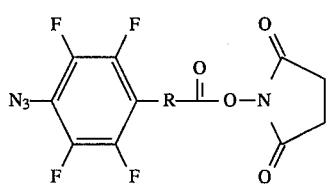

Other candidate aryl azides useful as functionalizing reagents are similar to the above examples except that another aryl moiety replaces the PFPA, such as:

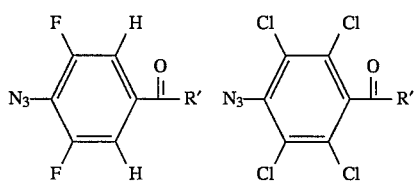

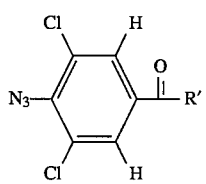

Candidate substrates that can be functionalized according to the present invention include, but are not limited to: polymeric substrates, graphite, metals, and siliceous materials; as well as silicon, gallium arsenide, and other semiconducting materials. Since the substrate comprises at least an analyte branch of an interferometer according to the present invention, it is of course necessary that the substrate exhibit a refractive index to the wavelength of light to be passed through the interferometer.

In the case of siliceous substrates (e.g., glass, silica, mica, quartz) it is believed that the functionalizing reagents, when converted to corresponding nitrenes, react with SiO—H groups, Si—OH groups, or Si—OSi groups on the substrate surface.

In the case of graphite and other allotrophic forms of elemental carbon, it is believed that the functionalizing reagents, when converted to the corresponding nitrenes, react with carbon rings on the substrate surface.

Polymeric substrates that can be functionalized according to the present invention include virtually any polymeric material comprising polymer molecules possessing —CH groups, and/or —NH groups, and/or —OH groups and/or —C=C— sites. Such polymeric substrates include, but are not limited to:

(a) saturated polyolefins as exemplified by polyethylene, polyvinyl chloride, polytetrafluoroethylene, polypropylene, polybutenes, and copolymers thereof;

(b) acrylic resins such as polymers and copolymers of acrylic acid, methacrylic acid [poly(methylmethacrylate), poly(hexylmethacrylate)], and acrylonitrile;

(c) polystyrene and its analogues such as poly(p-chlorostyrene) and poly(p-hydroxystyrene);

(d) unsaturated polyolefins such as poly(isoprene) and poly(butadiene);

(e) polyimides such as polyimide(benzophenone tetracarboxylic dianhydride/tetraethylmethylenedianiline);

(f) polyesters such as poly(trimethylene adipate) and poly(hexymethylene sebacate);

(g) conjugated and conducting polymers such as poly(3-alkylthiophene), poly(3-alkylpyrrole), and polyaniline;

(h) inorganic polymers such as poly(aryloxyphosphazene), poly[bis(trifluoroethoxy)phosphazene], polysilanes, and polycarbosilanes, siloxane polymers, and other silicon-containing polymers;

(i) organic metals (i.e., organic polymers with metallic properties) such as polycroconaines and polysquaraines, as described in *Chemical and Engineering News* (Aug. 31, 1992), p.8.

(j) organometallic polymers such as palladium poly-yne and ferrocene-containing polyamides; and (k) polysaccharides such as cellulose fibers, chitin, and starch.

Other polymer examples are listed in Table I, above.

Functionalization of a substrate surface can occur in one or more stages, depending upon which functional group(s) are to be attached to the surface; whether or not it is necessary to protect the functional groups from undesired reactions during attachment to the surface; and up on matters of convenience.

For example, in a two-stage functionalization protocol, each stage involves a different functionalizing reagent. The first stage involves a first functionalizing reagent such as a NHS-PFPA, which is converted during the course of the first-stage reaction to a nitrene intermediate. During the first stage using, for example, a polymeric substrate, the NHS active-ester groups on the NHS-PFPA molecules become covalently attached to surface polymer molecules by a reaction that can be generally indicated as follows shown in Scheme 1:

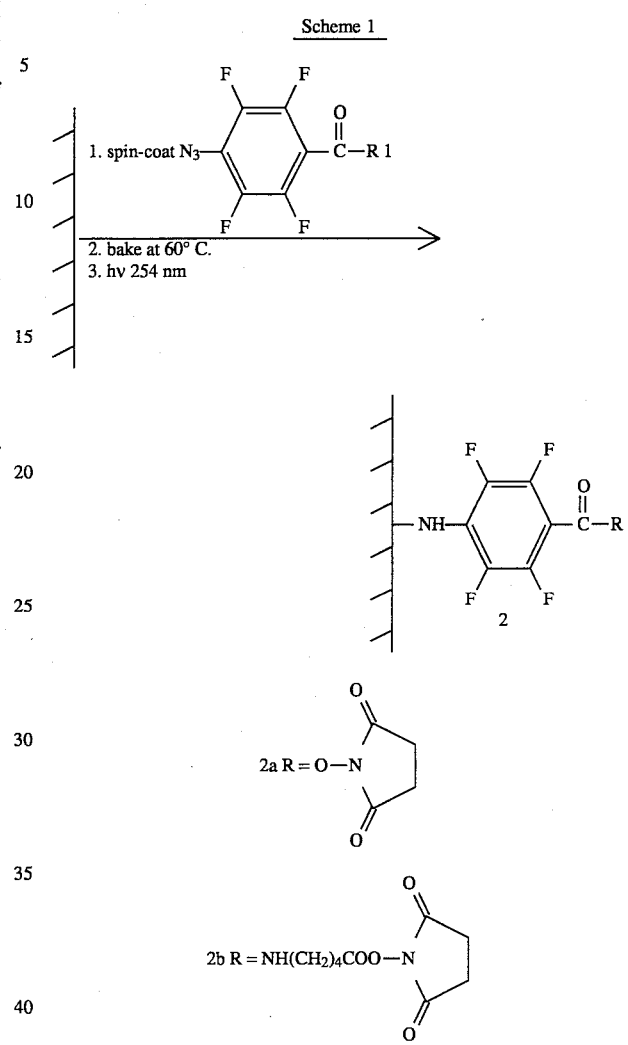

Thus, this first-stage reaction requires generation of a highly reactive nitrene intermediate derived from the NHS-PFPA 1 by exposure of the NHS-PFPA to a reaction-energy source.

As can be seen, the NHS-ester portions of the PFPAs do not participate in this first-stage chemistry. Rather, the NHS-esters, after being transferred to the surface molecules, are utilized in second-stage chemistry, discussed below.

In the second stage, the NHS esters readily react with molecules of a second functionalizing reagent. The second functionalizing reagent is selected from a group consisting of molecules possessing primary or secondary amines and/or hydroxyls. Reaction of NHS-esters with primary amines proceeds via amide formation as shown in Scheme 2:

Scheme 2

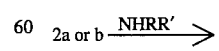

-continued
Scheme 2

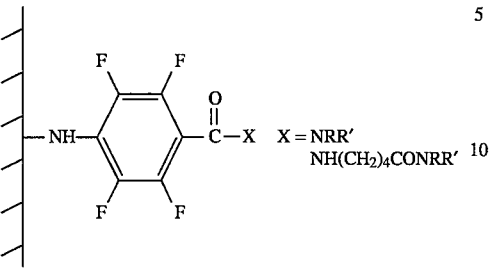

wherein compounds 2a and 2b are as shown in Scheme 1. Reaction of NHS-esters with hydroxyls proceeds via ester formation, as shown in Scheme 3:

Scheme 3

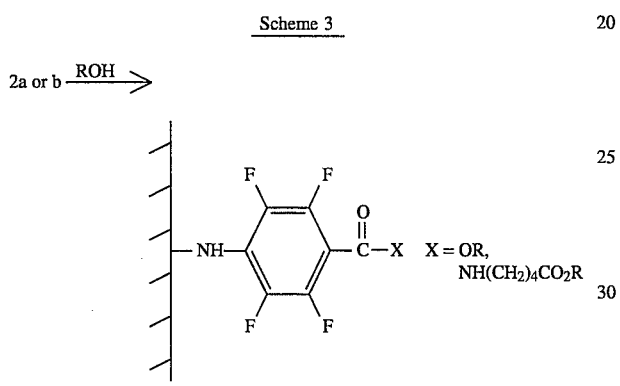

wherein compounds 2a and 2b are as shown in Scheme 1.

Since many types of biological molecules possess amine and/or hydroxyl groups, these molecules can serve as functionalizing reagents adapted for reaction in a second-stage functionalization reaction with HNS-esters covalently bonded to the surface molecules in a first-stage functionalization reaction. Thus, it is possible to attach any of a wide variety of molecules, including macromolecules such as proteins, nucleic acids, carbohydrates, and various other molecules, to substrates using methods according to the present invention.

It is also possible according to the present invention to first prepare nitrenogenic derivatives of molecules (such as biomolecules, drugs, analytes, catalysts [including transition metals], and diagnostic agents) to be attached to the substrate, apply the derivatives to a surface of the substrate, then expose the treated surface to a reaction-energy source to cause the nitrenogenic derivatives to covalently bond to surface molecules via nitrene intermediates. It is necessary for the nitrenogenic moiety to be structurally constrained such that the nitrene cannot readily react with another part of the same molecule. Thus, the 4-position of the phenyl ring is the preferred position for the azide group. To convey the scope of the present invention without intending in any way to be limiting, the following representative functionalizations according to the present invention are provided:

(a) Carcinogenic or mutagenic polycyclic aromatic hydrocarbons can be attached to a substrate to create a surface responsive to analytes normally reactive with these carcinogens or mutagens. Candidate polycyclic hydrocarbons include ethidium compounds and various pyrene compounds (such as 1-pyrenemethylamine and 6-aminochrysene). It is also possible, when attaching such compounds to a substrate, to employ "spacer groups"] serving to "lift" the hydrocarbon from the substrate surface. A representative spacer-containing hydrocarbon is the primary amine derived from 1-pyrenebutyric acid. Such reactions can be depicted generally as shown in Scheme 4:

Scheme 4

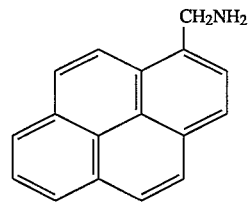

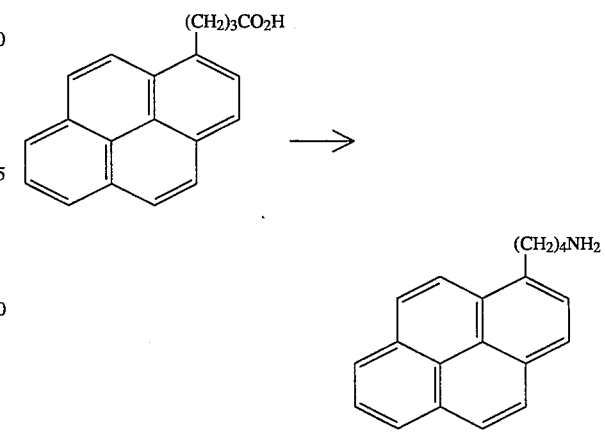

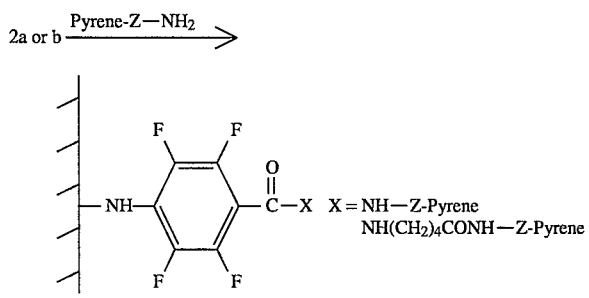

wherein 2a and 2b are as shown in Scheme 1 and 2 represents a spacer group.

(b) The hydrophobicity of a substrate surface can be altered, after attachment of NHS-ester groups to the substrate surface in a first-stage reaction (via a nitrene intermediate), by reaction of the NHS-ester groups with long-chain aliphatic amines such as 1-aminohexadecane in a second-stage reaction. Thus, the surface can be rendered more or less capable of bonding or otherwise interacting with a particular hydrophobic analyte. Such a reaction can be generally depicted as shown in Scheme 5:

Scheme 5

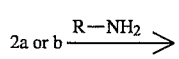

-continued
Scheme 5

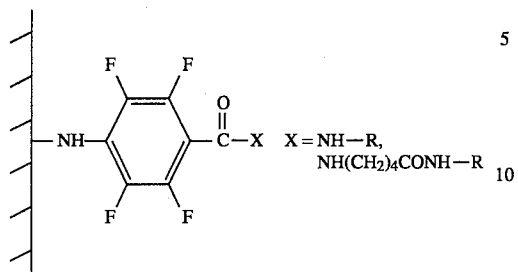

$X = NH-R,$
$NH(CH_2)_4CONH-R$ wherein R is a chain of hydrophobic atoms such as, for example, $C_{12}H_{25}-$, oleyl, octadecyl, 3-β-aminocholestane, or hexyldimethylsilyl; and 2a and 2b are as shown in Scheme 1.

(c) The hydrophilicity of the substrate surface can be altered, after attachment of NHS-ester groups to the substrate surface in a first-stage reaction (via a nitrene intermediate), by reaction of the NHS-ester groups with amine-possessing highly polar molecules in a second-stage reaction. Such amine-possessing polar molecules include (but are not necessarily limited to): glucosamine, ethanolamine, polyethyleneimine (protonated at pH 7), polylysine (also protonated at pH 7), glycerol, and other polyhydroxy compounds. Such reactions can be generally depicted as shown in Scheme 5 but wherein R is $HOCH_2CH_2-$, or $NH_2(CH_2CH_2NH-)_n-CH_2CH_2-$; and 2a and 2b are as shown in Scheme 1. For polyalcohols, such reactions can be generally depicted as shown in Scheme 6:

Scheme 6

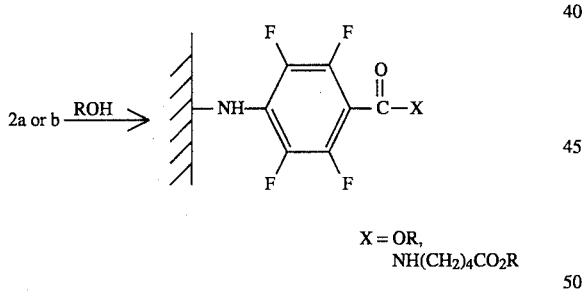

$X = OR,$
$NH(CH_2)_4CO_2R$ wherein R is, for example, $CH-CHOH-CH_2OH$; and 2a and 2b are as shown in Scheme 1.

(d) The substrate surface can be made surface-active in regions where NHS-ester groups have already been attached to the substrate surface in a first-stage reaction. The reaction to make surface-active proceeds by a second-stage reaction employing any of various aminated or hydroxylated "detergent" molecules such as, for example, 1-amino-dodecanoic acid. At pH 7 and after attachment of this compound to the substrate, the carboxyl group is ionized and the compound extends away from the substrate surface as a long hydrophobic tail terminating in a polar carboxylate anion. Such reactions can be generally depicted as shown in Scheme 7:

Scheme 7

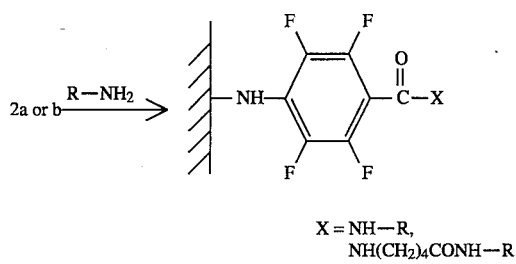

$X = NH-R,$
$NH(CH_2)_4CONH-R$ wherein R is $-(CH_2)_n-CO_2H$; and 2a and 2b are as shown in Scheme 1.

(e) Enzymes can be attached to a substrate surface functionalized in a first-stage reaction with, for example, an NHS active ester, by a second-stage reaction of, for example, a lysine amino group present on the enzyme molecules with the NHS active ester. Thus, the surface can be made to respond catalytically or conformationally to corresponding enzyme ligands. A representative reaction is depicted as shown in Scheme 8:

Scheme 8

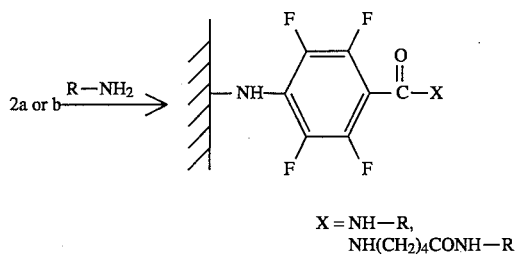

$X = NH-R,$
$NH(CH_2)_4CONH-R$ wherein $R-NH_2$ represents a lysine residue on a polypeptide such as an enzyme (e.g., horseradish peroxidase), lectin, or antibody; and 2a and 2b are as shown in Scheme 1.

(f) Antibodies, lectins, and other proteins can also be attached to substrates by functionalizing reactions similar to such reactions for attaching enzymes. Such molecules can then be used, when attached to the analyte branch(es) of interferometer according to the present invention, as selective sensing agents for analytes such as cells, cellular organelles, viruses, membrane constituents and other biological entities.

(g) Specialized molecules can be attached to a substrate surface to control the wettability of the substrate surface or alter the ability of living cells to adhere to the substrate surface.

(h) Substrate surfaces can be biotinylated in a one or two-stage reaction, followed by treatment of the biotinylated surface with, for example, a derivatized avidin or streptavidin. The avidin or streptavidin are thus used as bridging units for subsequent attachment of other biomolecules to the surface. Representative reactions are as follows:

Scheme 9
Two-stage reaction (Scheme 9)

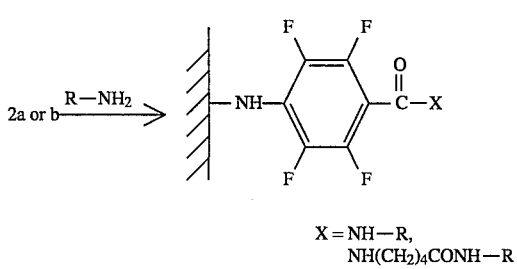

X = NH—R,
NH(CH₂)₄CONH—R wherein 2a and 2b are as shown in Scheme 1 and RNH₂ represents the amino group of N-biotinylhexylenediamine:

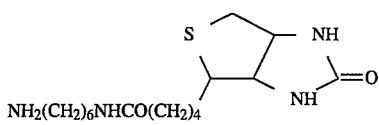

NH₂(CH₂)₆NHCO(CH₂)₄

A one-stage reaction is exemplified by coating the substrate with the PFPA derivatives of biotin (see Scheme 12, compound 5), followed by exposure to photolysis or an electron beam.

To further illustrate and describe the present invention, the following examples are provided:

EXAMPLE 1

In this Example, we modified the surface of a representative polymer (polystyrene) using N-hydroxysuccinimide-functionalized (NHS-functionalized) perfluorophenyl azides (PFPAs) 1a and 1b (Scheme 10).

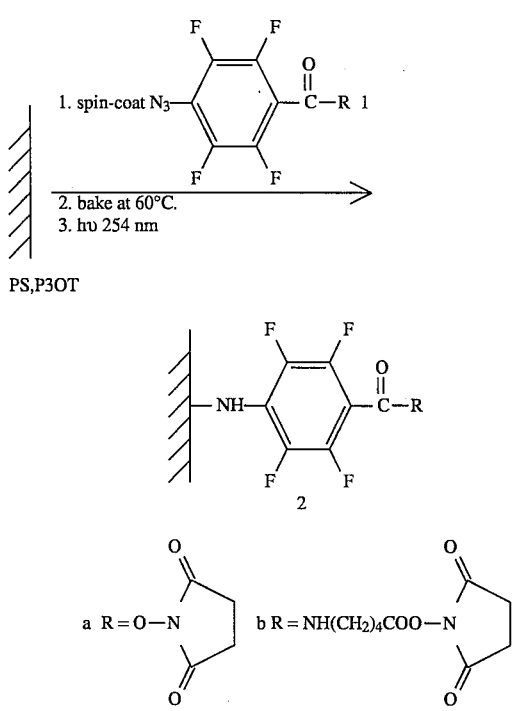

-continued
Scheme 10

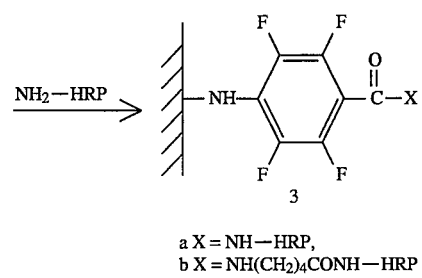

a X = NH—HRP,
b X = NH(CH₂)₄CONH—HRP

PFPA 1a is described in Keana et al., *J. Org. Chem.* 55:3640–3647 (1990).

PFPA 1b was prepared by N-acylation of 5-aminopentanoic acid with 4-azido-2,3,5,6-tetrafluorobenzamido) pentanoic acid (melting point (mp): 160°–161° C.; High-resolution mass spectrometry (HRMS) calculated for $C_{12}H_{10}F_4N_4O_3$: 334.0687; found m/z: 334.0710) which was then coupled with NHS in the presence of dicyclohexylcarbodiimide to yield N-succinimidyl 5-(4-azido- 2,3,5,6-tetrafluorobenzamido)pentanoate 1b (mp: 93°–95° C.; HRMS calculated for $C_{16}H_{13}F_4N_5O_5$: 431.0850; found m/z: 431.0866).

A glass disc was spin-coated with a solution of 5 wt % polystyrene (PS) in xylene to form a film on the disk about 0.5 μm thick, as described in Cai et al., *Chem. Mater.* 4:879–884 (1992). The PS film was then spin-coated with a solution of 0.5 wt % of 1a or 1b in nitromethane and baked at 60° C. for 20 minutes. The baking step removed residual solvent and likely facilitated the diffusion of surface-deposited PFPAs into the PS films.

Subsequent photolysis of the film resulted in complete decomposition of the azido groups as indicated by FTIR (Fourier-Transform Infrared) spectroscopy. Photolysis was carried out in a Rayonet photoreactor with 254-nm lamps for 5 minutes at ambient temperature under air. FTIR was performed with a control sample using a NaCl disc as the support. Covalent attachment of the NHS PFPA esters to the PS surface yielded 2a and 2b (Scheme 10), respectively. We believe that the reaction occurred via C—H bond insertion of the highly reactive nitrene intermediate derived from 1a or 1b. See, Keana et al., *J. Org. Chem.* 55:3640–3647 (1990); Leyva et al., *J. Org. Chem.* 54:5938–5945 (1989); and Poe et al., *J. Am. Chem. Soc.* 114:5054–5067 (1992).

Since NHS active esters react readily with primary and secondary amines to form amides, Anderson et al., *J. Am. Chem. Soc.* 86:1839–1842 (1964), a variety of primary and secondary amine-containing reagents including biomolecules may in principle be attached to the polymer surface by this method.

EXAMPLE 2

In this Example, we immobilized horseradish peroxidase (HRP, Sigma) on PS films modified by PFPA-NHS as described in Example 1. Compounds are shown in Scheme 10.

The films 2a and 2b were incubated in a 50-μM solution of HRP in NaHCO₂ buffer (pH 8.2) at 25° C. for 3 hours, Brinkley, *Bioconjugate Chem.* 3:2–13 (1992), followed by a thorough rinsing with phosphate buffer (pH 7.0). The enzyme activity of the resulting immobilized HRP films 3a and 3b was determined spectrophotometrically at 420 nm and 25° C. in phosphate buffer according using 2,2'-azino-bis(3-ethylbenzthiazoline-6-sulfonic acid) diammonium salt (ABTS) and hydrogen peroxide (1.8 mM ABTS/0.8 mM $H_2O_2$). Groome, *J. Clin. Chem. Clin. Biochem.* 18:345–349 (1980). Making the reasonable assumption that the immobilized HRP has the same activity as the native HRP, Nakane et al., *J. Histochem. Cytochem.* 22:1084–1091 (1974), the extent of immobilization of HRP was calculated to be $0.5\pm0.1$ ng/mm$^2$ for 3a and $1.0\pm0.2$ ng/mm$^2$ for the spacer-containing analogue 3b, indicating reasonable immobilization efficiencies.

An HRP molecule has a molecular weight around 40,000 daltons and a radius of 2.67 nm in the hydrated state. Steiner et al., *Eur. J. Biochem.* 82:543–549 (1978). Assuming a flat polymer surface, the surface coverage of a monolayer of HRP is 2.7 ng HRP per mm$^2$.

In control experiments, polymer films not spin-coated with PFPA were similarly baked, irradiated, and incubated with HRP solution. The resulting films showed no HRP activity.

EXAMPLE 3

In this Example, we performed surface modification of the conducting polymer, poly(3-octylthiophene) (P3OT), Cai et al, *J. Mol. Electron.* 7:63– 68 (1991), in a manner similar to the methodology described in Examples 1 and 2. The extent of immobilization of HRP on PFPA-NHS-modified P3OT films was $0.2\pm0.1$ ng/mm$^2$ with film 3a (Scheme 10) and $0.3\pm0.1$ ng/mm$^2$ with film 3b.

EXAMPLE 4

In this Example, we performed surface modification of a PS surface using PFPAs in combination with photolithography to generate micron-size patterns on the surface of the polymer. Compounds are as shown in Scheme 10.

A PS film was spin-coated with a nitromethane solution of 1a, baked as described above, and irradiated through a high-resolution photomask having a minimum feature size of 0.5 μm. Photolysis was carried out in a KSM Karl Suss deep-UV contact aligner. The film was then dipped in nitromethane for 20 seconds, air dried, and allowed to react with a solution of 5-(aminoacetamido)fluorescein (Molecular Probes, Inc., Eugene, Oreg.) in ethanol (4 mg/mL) at 25° C. for 1 hour followed by thorough rinsing with ethanol.

Figure 2:
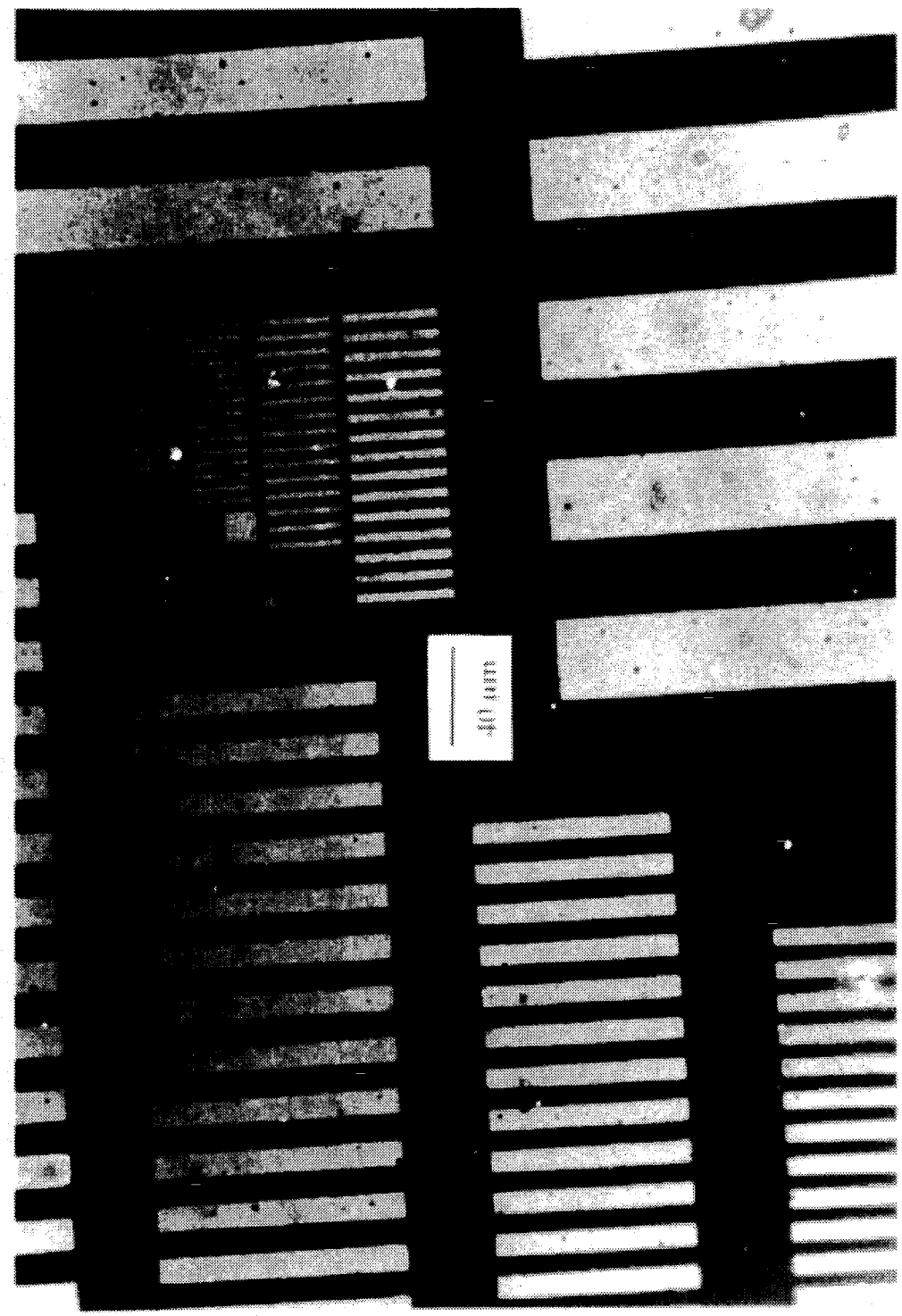
FIG. 2 is a photograph of micron-sized patterns as observed under a fluorescence microscope (450–490 nm excitation wavelength; >510 nm emission) showing the surface modification of a polystyrene film as described in Example 4.

FIG. 2 shows the resulting micron-size patterns as observed under a fluorescence microscope, further demonstrating this new surface modification strategy. The smallest features (0.5 μm) are resolved but are slightly broadened, probably owing to diffraction effects.

As a control, a PS film without spin-coating NHS active ester 1a was photolyzed, developed and treated with 5-(aminoacetamino)fluorescein. No fluorescent patterns were observed under the fluorescence microscope (data not shown).

EXAMPLE 5

In this Example we modified the surface of a preformed polymer microstructure. Compounds are as shown in Scheme 10.

A micron-scale pattern of PS, which had previously been fabricated on a silicon wafer using deep-UV lithography, was dipped in a nitromethane solution of 1a for 10 seconds, baked, and photolyzed as described above. The sample was then immersed in a solution of N-(5-aminopentyl) biotinamide (Molecular Probes, Inc., Eugene, Oreg.) in DMF (1 mg/0.2 mL) for 4 h, and washed with DMF followed by ethanol. Taking advantage of the strong affinity of avidin for biotin (Green, *Adv. Protein Chem.* 29:85–133 (1975); Heitzmann et al., *Proc. Nat. Acad. Sci. U.S.A.* 71:3537–3541 (1974)), fluorescein-avidin (Molecular Probes, Inc., Eugene, Oreg.) was attached to the surface by incubating the wafer in a solution of the fluorescent protein in pH 8.2 buffer (3.2 mg/0.5 mL) for 4 h.

Figure 3A:
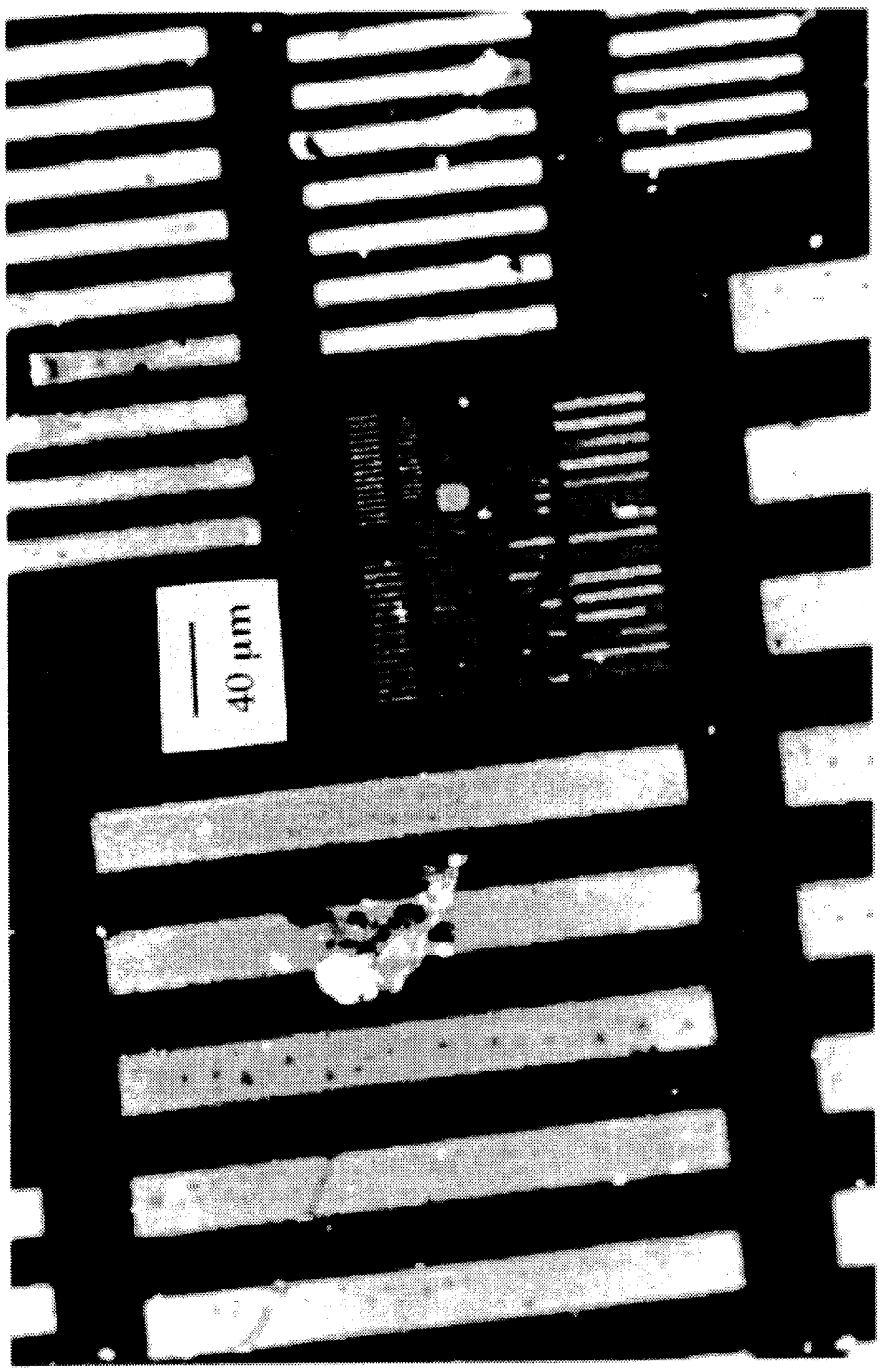
FIG. 3A is a photomicrograph of fluorescent protein formed by treating preformed polystyrene patterns with a PFPA compound (compound 1a in Scheme 1) followed by photolysis, then treating with N-(5-aminopentyl)biotinamide followed by fluorescein-avidin, as described in Example 5.
Figure 3B:
FIG. 3B is a photomicrograph of an experimental control wherein polystyrene patterns were treated with fluorescein-avidin only, as described in Example 5.

The resulting micron-size patterns are shown in FIG. 3A and the experimental control is shown in FIG. 3B. These results indicate that the biotin-avidin-fluorescein assembly became covalently attached to the preformed PS microstructure.

EXAMPLE 6

In this Example, we functionalized the surface of graphite. A piece of pyrolytic graphite was freshly cleaved using transparent adhesive tape and coated with a solution of 0.5 % w/w N-hydroxysuccinimidyl 4-azidotetrafluorobenzoate (NHS-PFPA) in dry nitromethane by spinning at a speed of 1000 rpm. The coated graphite was baked at 60° C. for 20 minutes and irradiated for 5 minutes using 254-nm lamps at ambient temperature under air. The graphite was then incubated in a 50-μM solution of horseradish peroxidase (HRP) in $NaHCO_3$ buffer (pH 8.2) at 25° C. for 3 hours and rinsed thoroughly with phosphate buffer (pH 7.0).

The enzymatic activity of the functionalized graphite was determined spectroscopically at 420 nm and 25° C. in phosphate buffer using 2,2'-azino-bis( 3-ethylbenzthiazoline-6-sulfonic acid) diammonium salt (ABTS) and hydrogen peroxide (1.8 mM ABTS/0.8 mM $H_2O_2$). Assuming that the immobilized HRP had the same activity as the native HRP, the extent of immobilization of HRP was 2.1 ng/mm$^2$.

A control experiment was performed as follows: A piece of freshly cleaved graphite was similarly baked, irradiated, and incubated with HRP solution. The enzyme-activity of the control was determined to be 0.4 ng HRP/mm$^2$. Thus, the control was not treated with NHS-PFPA.

Samples and controls were examined using atomic-force microscopy (AFM). The atomic-force microscope was operated in air at ambient temperature.

Figure 4A:
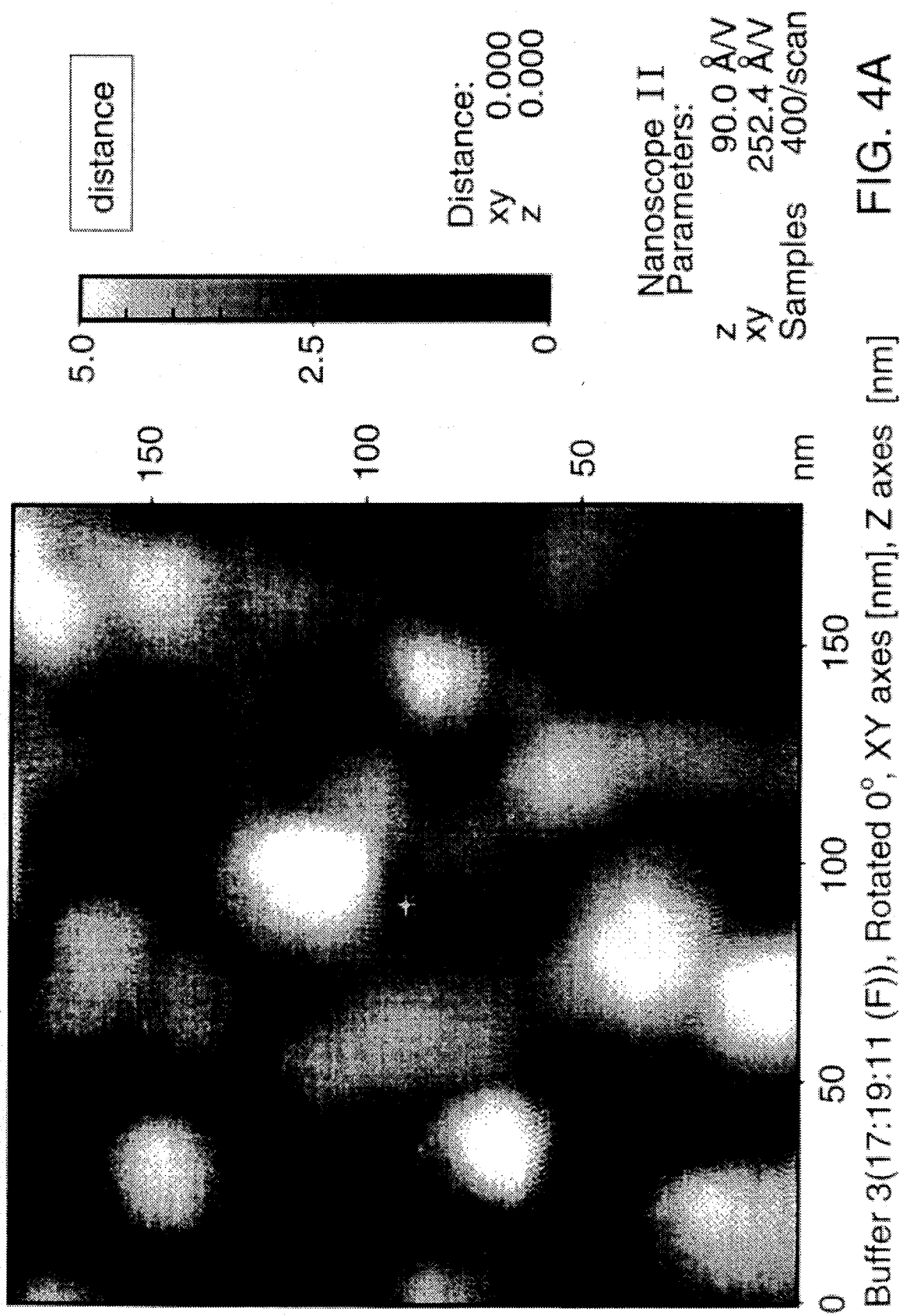
FIG. 4A is an image obtained with an atomic-force microscope of a freshly cleaved graphite surface functionalized first with NHS-PFPA, then with horseradish peroxidase, as described in Example 6.
Figure 4B:
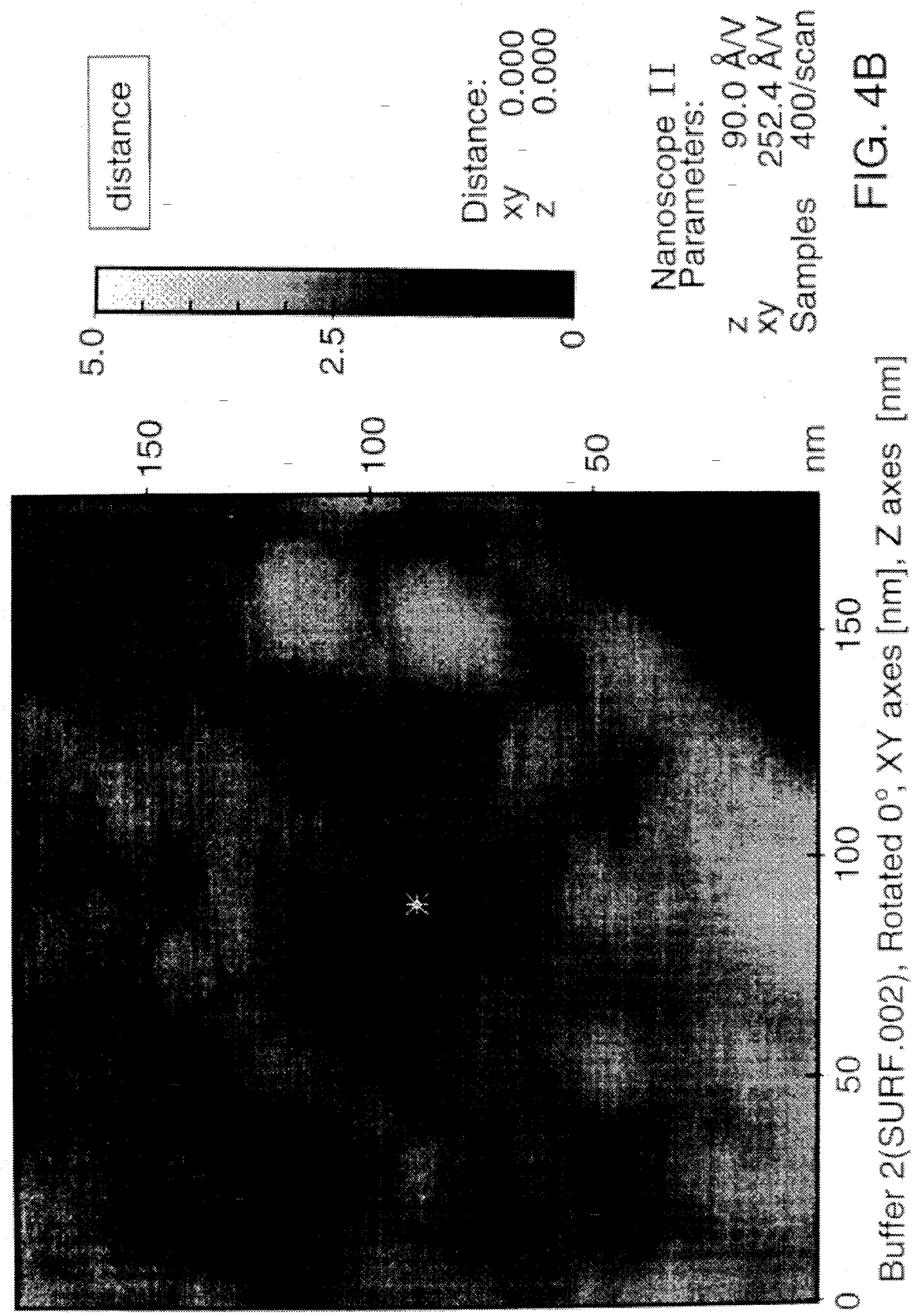
FIG. 4B is an atomic-force microscope image of an experimental control wherein a freshly cleaved graphite surface was treated with horseradish peroxidase but not with NHS-PFPA, as described in Example 6.

A representative AFM image of the sample is shown in FIG. 4A and of the control in FIG. 4B. In FIG. 4A, bright spheres correspond to immobilized HRP molecules. In FIG. 4B, only a few faint spheres were seen, indicating much less immobilization of the HRP molecules to the control surface.

Therefore, the NHS-PFPA is necessary to achieve substantial covalent attachment of HRP to the graphite surface.

EXAMPLE 7

The chemistry of this Example is illustrated in Scheme 11, wherein two photoactive biotins, PFPA-biotins 3 and 5 were prepared. These photoactive biotins could be used to functionalize a polymer surface with biotin groups. Such biotinylated surfaces can be further reacted so as to attach biomolecules to the substrate through biotin-binding proteins such as avidin.

Scheme 11

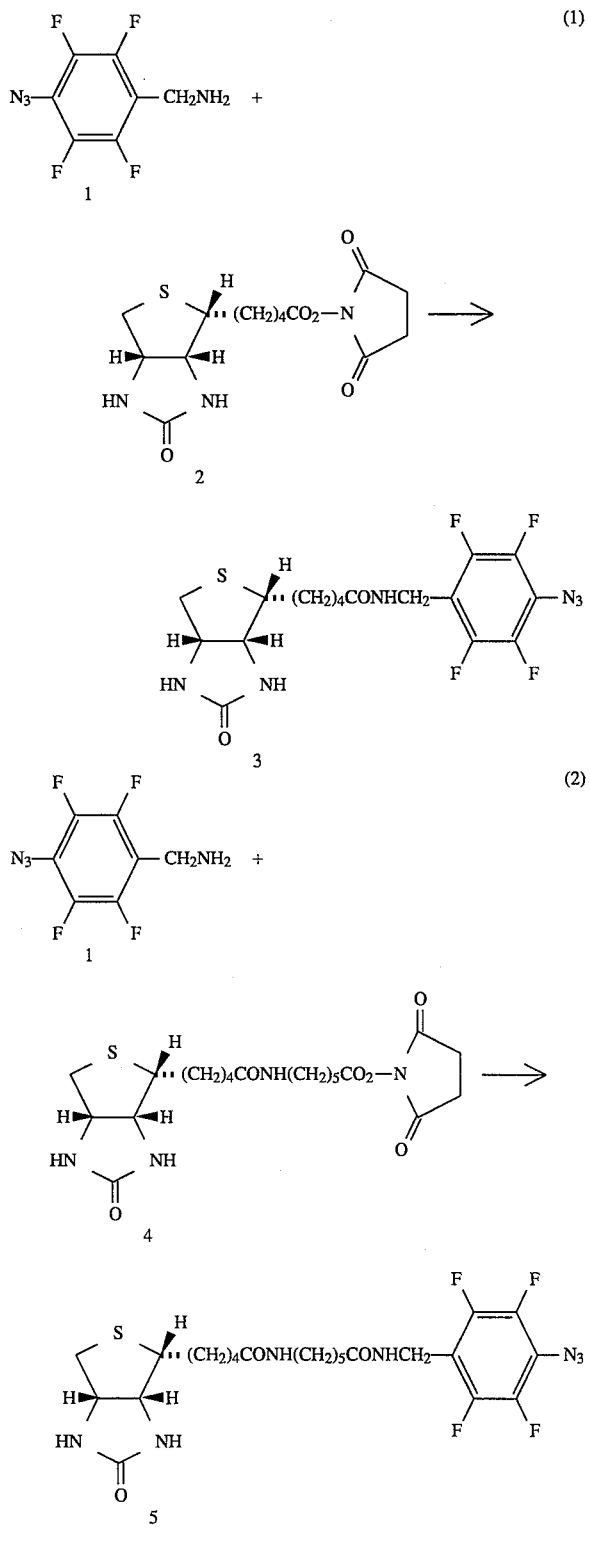

revealed completion of the reaction. The solution was added dropwise into 10 mL water to form a precipitate. The precipitate was filtered, washed with water, and dried to yield 36.8 mg (85%) of 3 as an almost colorless solid having a mp=164°–165° C. $^1$H-NMR (CDCl$_3$+DMSO)-d$_6$): 1.157 (q,2), 1.40 (m,4), 1.950 (t,2), 2.87 (m,2), 4.01 (m,1), 4,20 (m,3), 5.41 (m,2), 7.53 (m,1). IR (KBr): 3454, 3290, 2931, 2161, 2125, 1704, 1654, 1549, 1493, 1420, 239, 1054 cm$^{-1}$.

Synthesis of N-4-azido-2,3,5,6-tetrafluorobenzyl- 6-(biotinamido)hexanamide (5) was performed as follows: To a solution of 49.2 mg (0.108 mmol) of N-succinimidyl-6-(biotinamido)hexanoate in 0.6 mL of dry DMF was added 32 mg (0.14 mmol) of 4-azido-2,3,5,6-tetrafluorobenzylamine. The solution was stirred at room temperature for one hour, then added dropwise into 10 mL water. The resulting precipitate was filtered, washed by water, and dried to yield 60.1 mg (99%) of 5 as a colorless solid with mp= 160°–161° C. $^1$H-NMR (CDCl$_3$+DMSO-d$_6$): 0.98 (m,2), 1.14 (m,4), 1.31 (m,6), 1.85 (m,4), 2.4–2.5 (m,2), 2.8 (m,3), 3.92 (m,1), 4.10 (m,3), 5.52 (s,1), 5.56 (s,1), 6.76 (m,1), 7.56 (m,1). IR (KBr): 3438, 3301, 2935, 2162, 2177, 1700, 1652, 1547, 1499, 1416, 1239, 1054 cm$^{-1}$.

EXAMPLE 8

This Example pertains to the synthesis of several PFPA-based cross-linkers capable of functionalizing polymers. In particular, a group of NHS-ester functionalized PFPAs with different linker lengths between the NHS ester group and the PFPA group were synthesized. These functionalized PFPAs were particularly adapted for photo-cross-linking amino groups in biopolymers to proximally located chemical groups and for functionalization of polymers in general. The overall chemistry is diagrammed in Scheme 12.

Scheme 12

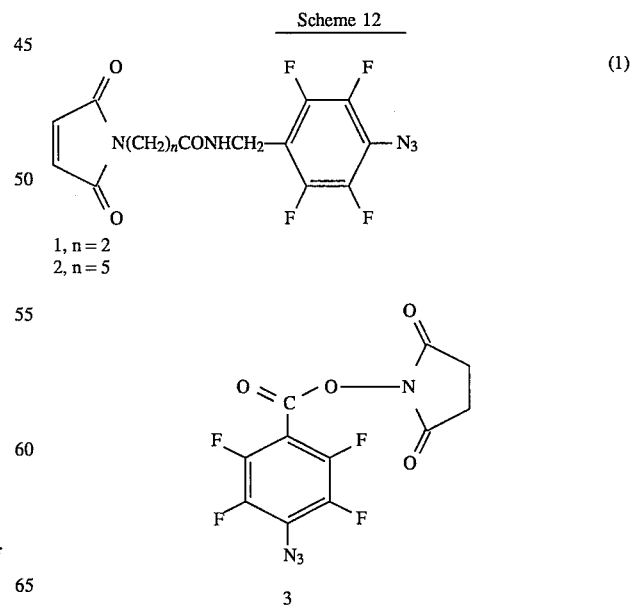

Synthesis of N-4-azido-2,3,5,6-tetrafluorobenzyl biotinamide (3) was performed as follows: To a solution of 33 mg (0.097 mmol) N-succinimidyl-D-biotin in 0.5 mL of DMSO-d$_6$ was added 27 mg (0.12 mmol) of 4-azido-2,3,5, 6-tetrafluorobenzylamine. The resulting solution was maintained at room temperature for 0.5 hours, after which NMR

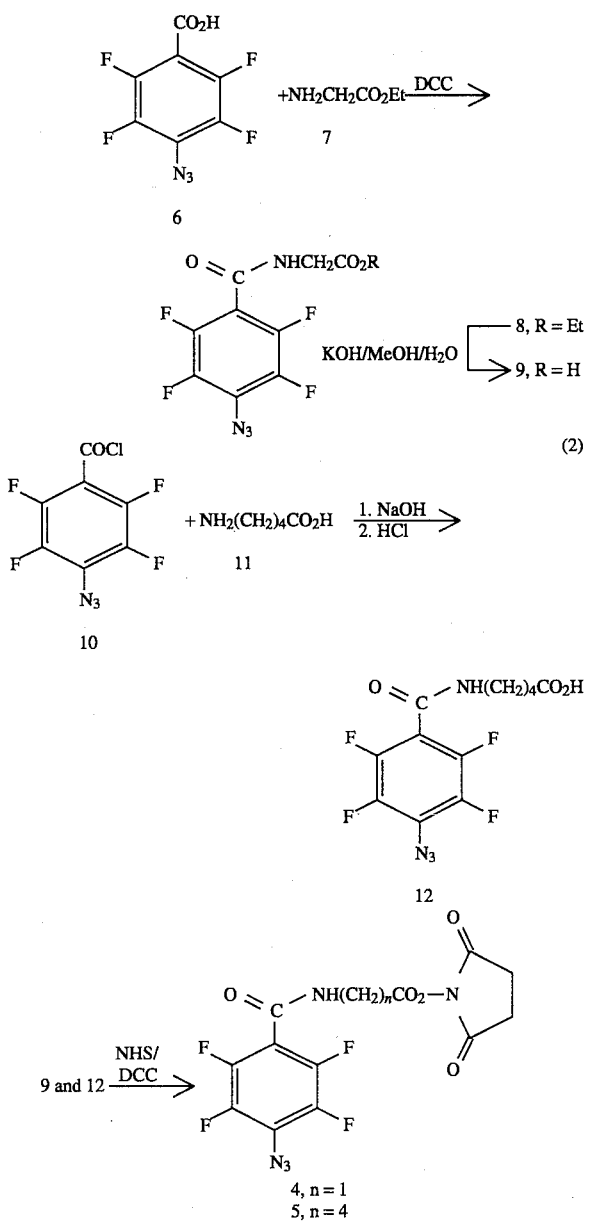

The chemistry utilizes maleimide-containing PFPAs 1 and 2 which were previously used to map cysteine residues introduced into ATPase by mutation, yielding a photo-crosslinking yield as high as 50 percent. Aggeler et al., *Biochemistry* 31:2956–2961 (1992).

The NHS-containing PFPAs 4 and 5 are particularly adapted for cross-linking of an amino group in a polypeptide chain to a proximally located chemical group by means of a photochemical —CH or —NH insertion reaction. These PFPAs can also be used to modify polymers with the NHS groups which can then be reacted with amino-containing reagents for introducing other functional groups into the polymers.

In Scheme 12, reaction of acid 6 and the glycine ethyl ester 7 with dicyclohexylcarbodiimide (DCC) as coupling reagent produced the amide 8 as follows: A mixture of 217 mg (1.55 mmol) of glycine ethyl ester hydrochloride and 158 mg (1.56 mmol) of triethylamine in tetrahydrofuran (7 mL) was stirred for 20 minutes. Afterward, 369 mg (1.57 mmol) of 4-azido-2,3,5,6 tetrafluorobenzoyl acid 6 and 324 mg DCC was added. The mixture was stirred overnight and filtered. The filtrate was evaporated and the residue dissolved in 20 mL of ethyl acetate. The solution was then dried and filtered. The filtrate was washed with 0.1N HCl (2×10 mL), 5% NaHCO$_3$ (2×10 mL), and water (2×10 mL). The solution was dried and evaporated to yield a solid that was purified by preparative TLC to yield 160 mg (32% yield) of 8 as a colorless solid with a mp=85°–86° C. $^1$H NMR: 1.321 (t,3, J=7.13), 4.239 (d,2, J=4.82), 4.273 (q,2, J=7.13), 6.540 (mb,1). IR: 2128, 1744, 1686, 1649, 1523, 1488, 1225, 1001 cm$^{-1}$. Anal. calcd for C$_{11}$H$_8$F$_4$N$_4$O$_3$: C, 41.26; H, 2.52; N, 17.50. Found: C, 41.46; H, 2.37; N, 17.66.

Subsequent hydrolysis produced the acid 9 as a solid in 31% overall yield, as follows: To a solution of 60 mg of 8 in 0.5 mL methanol was added 0.4 mL of a solution of 2.5% aqueous NaOH. The resulting solution was stirred for one hour. The solution was then acidified to pH<1 using 2N HCl. The precipitate was filtered and dried to yield 23 mg of 9 as a white solid. The filtrate was extracted by THF/CHCl$_3$ (1:1, 3×3 mL) and the extract was dried and evaporated to yield a further amount (32 mg) of 9 as a white solid (combined yield 55 mg, 99%) with a melting point of 147°–148° C. $^1$H-NMR (CDCl$_3$+DMSO-d$_6$): 4.339 (d,2, J=4.80), 6.527 (m,1). MS: 292 (2, M$^+$), 264 (20, M$^+$-N$_2$), NC$_6$F$_4$CO) 162 (100, NC$_6$F$_4$).

Reaction of the acyl chloride 10 with 5-aminopentanoic acid 11 under basic conditions followed by acidification produced the acid 12, as follows: To a solution of 238 mg (2.03 mmol) of 5-aminopentanoic acid 11 in 50% aqueous NaOH (0.4 mL) and 2.6 mL water was added 239 mg (0.942 mmol) of 4-azido-2,3,5,6-tetrafluorobenzoyl chloride 10. A precipitate was observed immediately. The mixture was stirred for 5 min and diluted with 3 mL water. The mixture was then stirred for another 15 minutes and acidified to pH<1 using 2-NHCl. The precipitate was filtered and washed with 0.1N HCl (1 mL) and 2 mL water, and dried to yield 231 mg of solid. The solid was washed using 1 mL ether and crystallized in a mixture of tetrahydrofuran and ether to yield 171 mg (54% yield) of 12 as a colorless solid with mp=160°–161° C. $^1$H-NMR (CDCl$_3$+DMSO-d$_6$): 1.753 (m,4), 2.540 (t,2, J=6.73), 3.504 (q,2, J=5.90), 6.1 (m,1) MS: 334 (5, M$^+$), 317 (4, M$^+$-OH) 306 (40, M$^+$-N$_2$) 190 (15, NC$_6$F$_4$CO) 162 (100, NC$_{64}$). High-resolution MS calc'd for C$_{12}$H$_{10}$F$_4$N$_4$O$_3$: 334.0687; found: 334.0710.

The NHS-active esters 4 and 5 were prepared by reaction of acids 9 and 12 with N-hydroxysuccinimide in the presence of DCC, respectively. In particular, to prepare 4, a solution of 39.3 mg (0.134 mmol) of 9, 29.3 mg (0.142 mmol) of DCC, and 16.6 mg of NHS in 0.5 mL THF was stirred at 25° C. overnight. The resulting mixture was filtered. The filtrate was evaporated to yield a solid that was redissolved in 1 mL CH$_2$Cl$_2$. The resulting mixture was filtered. The filtrate was evaporated to yield 42 mg (80% yield) of 4 as a colorless solid. The analytical sample was obtained via recrystallization in acetone/hexane as a colorless solid having a mp=145°–146° C. $^1$H-NMR: 2.883 (s,4), 4.637 (d,2, J=5.40), 6.548 (mb,1). IR: 2129, 1792, 1748, 1718, 1699, 1649, 1520, 489, 1204 cm$^{-1}$. MS: 389 (8, M$^+$), 275 (60 M$^+$-NHS), 247 (27, M$^+$-NHS-N$_2$) 218 (65, M$^+$-CONHS-N$_2$-H), (45, NC$_6$F$_4$CO), 162 (100, NC$_6$F$_4$). High-resolution MS calculated for C$_{13}$H$_7$F$_4$N$_5$O$_5$: 389.0382; found: 389.0405.

NHS ester 5 was prepared from acid 12 in a manner similar to ester 4 and was isolated as a colorless solid at 91% yield having a mp=93°–95° C. $^1$H-NMR: 1.77 (m,2), 1.85 (m,2), 2.691 (t,2, J=6.65), 2.841 (s,4), 3.512 (q,2, J=6.24), 6.22 (m,1). IR: 2127, 1817, 1786, 1742, 1681, 1649, 1602, 1526, 1487, 1260, 1209, 1069 cm$^{-1}$. MS: 431 (5, M$^+$), 403 (3, M$^+$-N$_2$), 317 (22, M$^+$-NHS), 289 (8, M$^+$-NHS-N$_2$), 162 (100, NC$_6$F$_4$). High-resolution MS calcd for C$_{16}$H$_{13}$F$_4$N$_5$O$_5$: 431.0850; found: 431.0866.

The two NHS-active esters 4 and 5, together with NHS-active ester 3, formed a group of NHS-containing PFPAs having linkers of different lengths between the PFPA and the NHS groups. Thus, compounds 3, 4, and 5 are useful for functionalizing amino groups in biopolymers such as polypeptide chains via the NHS group and subsequent crosslinking to a proximally located biopolymer by photo-generated nitrene intermediates. The compounds can also be used for functionalizing substrates, including polymeric substrates.

EXAMPLE 9

This Example is similar to Example 8, except that two heterobifunctional and cleavable PFPA-based crosslinkers were synthesized, as shown generally by the formula:

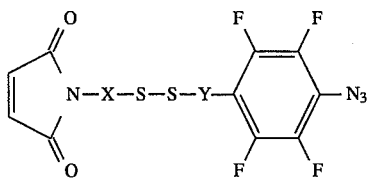

For example, the following compound was synthesized:

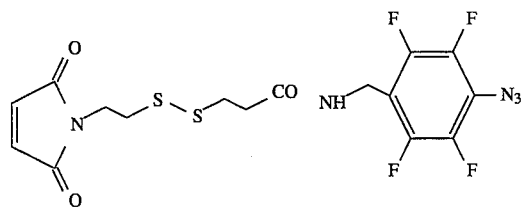

In general, the PFPA portion of the molecule can be used to functionalize a substrate, allowing the maleimide portion to be used for attaching another functional group (via reaction with an SH— containing molecule or a 1,3-diene-containing molecule in a Dieis-Alder type reaction.) Then, at a later time, the maleimide side can be cleaved from the surface under mild conditions. Another cleavable group can be a 1,2-diol linkage cleavable using periodic acid.

EXAMPLE 10

This Example pertains to the functionalization of polystyrene.

A 1-cm$^2$ piece of silicon wafer was coated with a solution of 5% w/w polystyrene by spinning at 1000 rpm. The wafer was then spin-coated with a solution of 0.5% w/w of N-hydroxysuccinimidyl-4-azido-2,3,5,6-tetrafluorobenzoate in nitromethane at a speed of 1000 rpm, baked at 60° C. for 20 minutes, and subjected to electron-beam lithography. The coated wafer was dipped in nitromethane for 20 seconds to remove any unattached PFPA, air dried, and allowed to react with a solution of 2 mg/mL 5-(aminoacetamido) fluorescein in ethanol at 25° C. for 1 hour. The wafer was then immersed in ethanol overnight to remove the non-covalently attached fluorescein residues.

Figure 5A:
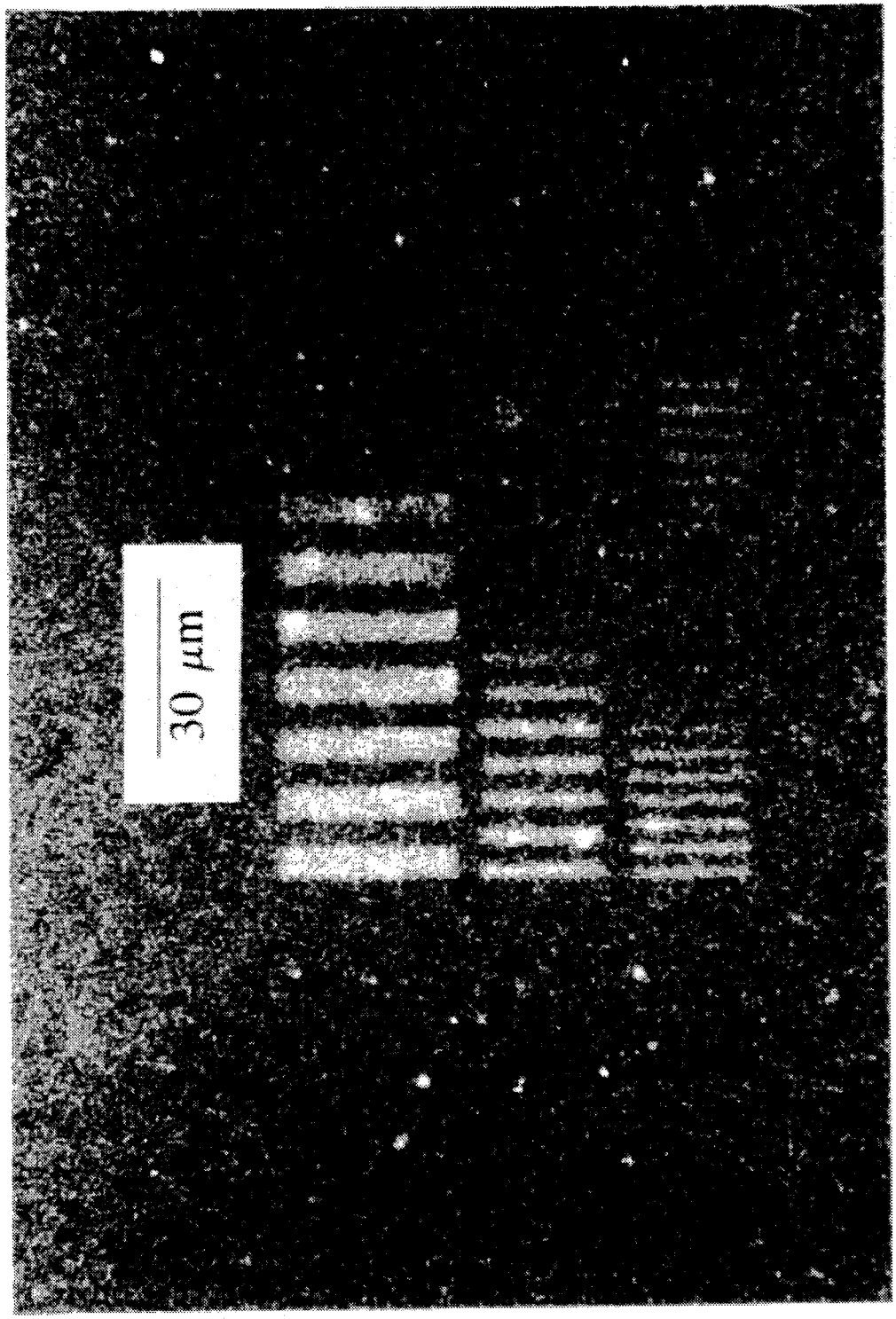
FIG. 5A is a photomicrograph obtained using a fluorescence microscope (450–490 nm excitation wavelength; >510 nm emission wavelength) of a polystyrene surface functionalized with NHS-PFPA using an electron beam as a reaction-energy source, as described in Example 10.
Figure 5B:
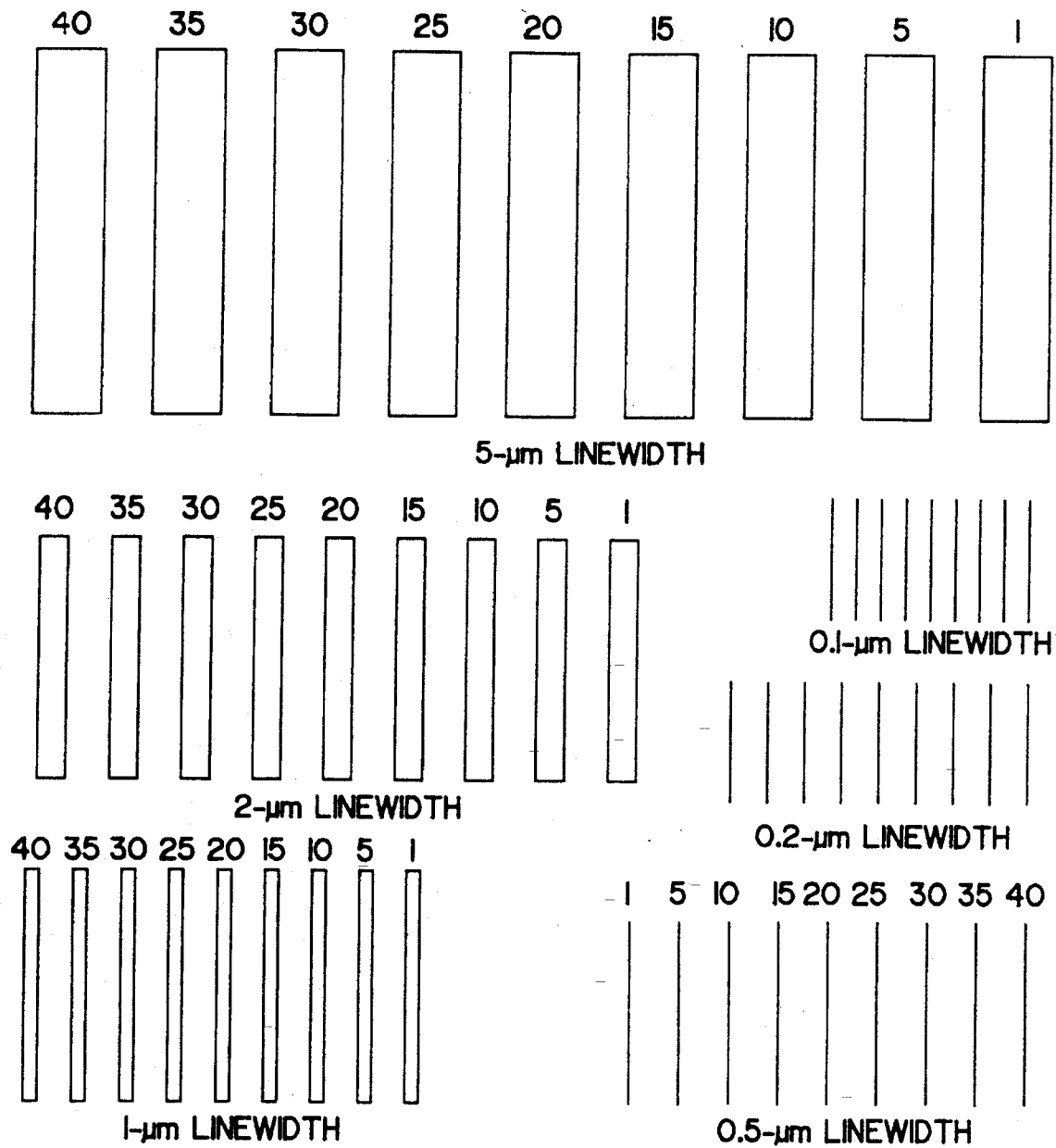
FIG. 5B is a legend for FIG. 5A showing beam dosages and linewidths.

The results are shown in FIG. 5A (legend in FIG. 5B), depicting patterns observed under a fluorescence microscope (450–490 nm excitation, >510 nm emission). The patterns were delineated by electron-beam lithography with the line widths of (from thickest to thinnest): 5 μm, 2 μm, 1 μm, 0.5 μm, 0.2 μm, and 0.1 μm (FIG. 5B). As shown in FIG. 5B, the dosages are 40, 35, 30, 25, 20, 15, 10, 5, and 1 μC/cm$^2$ from left to right for the 5, 2, and 1 μm widths and from right to left for the 0.5, 0.2, and 0.1 μm widths.

In FIG. 5A, features of 0.2 μm were resolved. The smallest features (0.1 μm) were not resolved in this unoptimized experiment. The sensitivity is about 10 to about 30 μC/cm$^2$.

EXAMPLE 11

In this example, polystyrene wave guides were fabricated on a silicon wafer coated with SiO$_2$. The coated silicon wafer was first cleaned in acetone. Then, the wafer was spin-coated with 5% w/w polystyrene (PS) and 4.6% (w/w relative to the PS) bis-perfluorophenyl azide (cross-linker) in xylene. the spin coating was performed at 4000 rpm for 25 seconds. The wafer was then baked at 70° C. for 30 minutes.

A 15 kV electron beam was used to delineate the wave guide structures in the PS film with dosages in the range of 5 to 30 μC/cm$^2$. Alignment marks were also exposed on the wafer for use during subsequent functionalization procedures. The electron beam causes the areas of the PS contacted thereby to become sufficiently crosslinked so as to be insoluble during a subsequent solvent-washing step.

After exposure to the electron beam the film was developed in xylene for 20 seconds to remove all PS not exposed to the electron beam, washed in IPA, then blow-dried using nitrogen gas.

Figure 6:
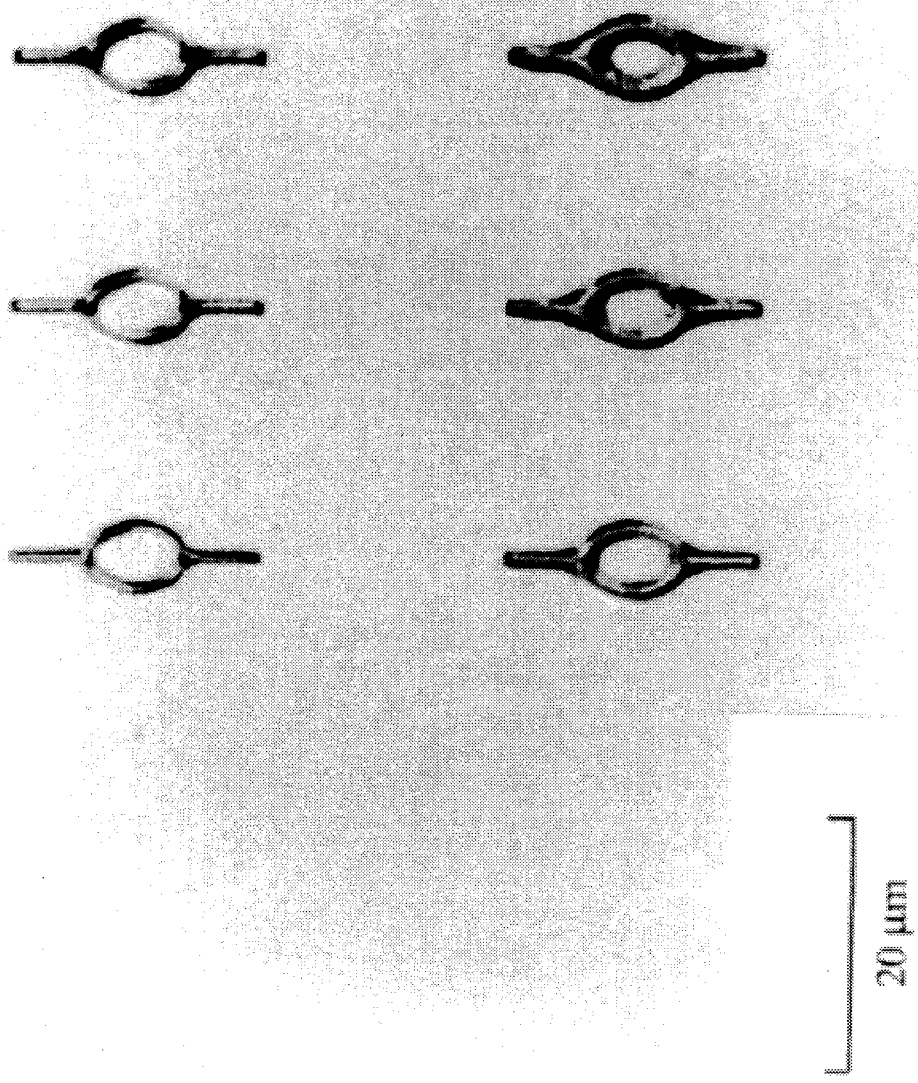
FIG. 6 is a photograph pertaining to Example 11 showing six waveguides fabricated from polystyrene on a silicon support/material.

We found that a dose of 10 μC/cm$^2$ yielded the best waveguide structure with these films. These waveguides had a thickness of about 500 nm and a width of about 1 μm. FIG. 6 shows six waveguides fabricated from PS. Electron-beam dosages, from the top left to the bottom right, respectively, were 5, 10, 15, 20, 25, and 30 μC/cm$^2$.

The physical dimensions of the waveguides are easily modified according to the intended use of the waveguides.

The fabricated PS waveguide structures were functionalized by first spin coating the wafer supporting the fabricated PS waveguide structures with 0.5% w/w perfluorophenyl azide (PFPA) solution in nitromethane using the same spin parameters as set forth above. The film was then baked at 70° C. for 30 minutes. Using the alignment marks to align an electron beam to the waveguides, only one branch (to become the analyte branch) of each waveguide was exposed to 15-kV electrons at a dosage of 20 μC/cm$^2$. The film was then developed in nitromethane for 20 seconds and blow-dried in nitrogen. Thus, only the analyte branch of each waveguide was functionalized.

The functionalized branches of the waveguides were rendered visible by immobilizing fluorescein on the functionalized branches and viewing the waveguides under a fluorescence microscope. Fluorescein was immobilized by immersing the wafer in a solution of 5-(aminoacetamido)fluorescein in NaHCO$_3$ buffer (pH 8.2; 0.4 mg/0.5 mL) for 3 hours. The film was then washed thoroughly with the buffer and air-dried. The film was then illuminated using the fluorescence microscope at 450– 490 nm. The resulting emissions at >510 nm were readily visible.

Figure 7:
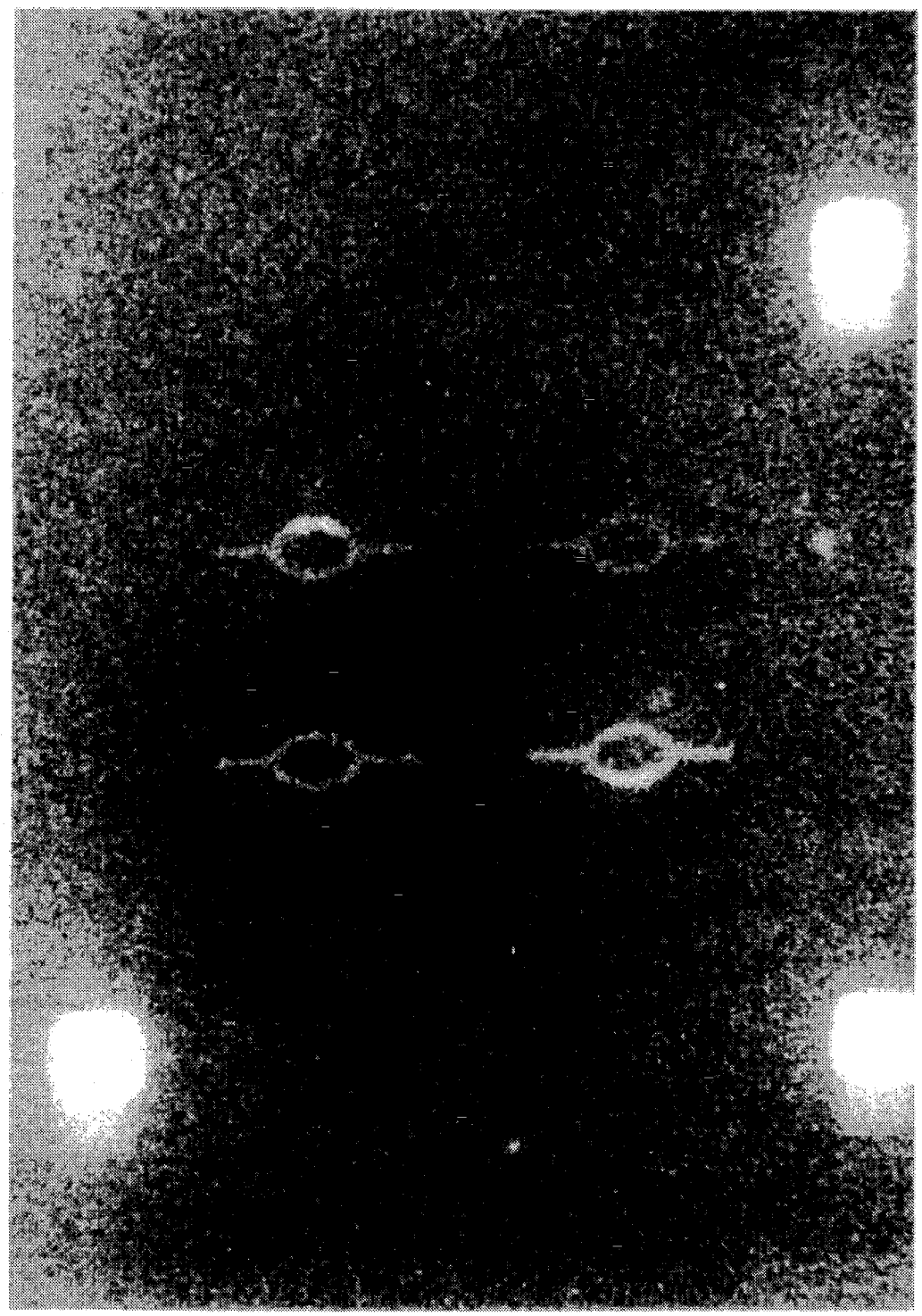
FIG. 7 is a photograph pertaining to Example 11 showing polystyrene interferometers, two of which having analyte branches functionalized with fluorescein, and visualized using a fluorescence microscope.

FIG. 7 shows two functionalized polystyrene interferometers and two controls on a single silicon wafer as viewed by fluorescence microscopy. The interferometers on the top right and bottom left are functionalized as described above. The other two are controls lacking functionalization. Functionalization is evidenced by the presence of fluorescence on the analyte branch (right branch in the top-right interferometer and left branch in the bottom-left interferometer). The large bright spots in three corners of the photograph are alignment marks.

The waveguides formed in this Example are classified as ridge waveguides. Of importance for transmission loss in these devices is their edge roughness. See, Tein, *Appl. Optics* 10:2395 (1971). We estimate the edge roughness of these waveguides to be about 50 nm.

Coupling light into and out of the waveguides can be achieved using the known techniques of prism coupling or grating coupling.

While the invention has been described in connection with preferred embodiments and multiple examples, it will be understood that it is not limited to those embodiments. On the contrary, it is intended to cover all alternatives, modifications, and equivalents as may be included within the spirit and scope of the invention as defined by the appended claims.

What is claimed is:

1. A sensor element, comprising:
   (a) an optical waveguide comprising a reference waveguide portion and an analyte waveguide portion both made of a material exhibiting an index of refraction to an electromagnetic radiation and both having a first end and a second end;
   (b) means for introducing the electromagnetic radiation into the first ends such that the electromagnetic radiation passes in parallel through the reference and analyte waveguide portions from the first ends to the second ends by total internal reflection;
   (c) means for converging the electromagnetic radiation at the second ends into an exit beam of the electromagnetic radiation; and
   (d) the analyte waveguide portion having an external surface that is functionalized relative to the reference waveguide portion so as to enable the external surface of the analyte portion to selectively interact with molecules of an analyte in a manner that imparts a phase change to the electromagnetic radiation passing through the analyte waveguide portion relative to the electromagnetic radiation passing through the reference waveguide portion, the phase change being sufficient to generate a corresponding interference pattern in the exit beam.

2. A sensor element, comprising an optical waveguide comprising an incoming waveguide portion, a reference waveguide portion, an analyte waveguide portion, and an outgoing waveguide portion, the optical waveguide being made of a material exhibiting an index of refraction to an electromagnetic radiation, the reference and analyte portions each having a first end coupled to the incoming waveguide portion and a second end coupled to the outgoing waveguide portion so as to enable the optical waveguide to pass electromagnetic radiation entering the incoming waveguide portion through, by total internal reflection, the incoming waveguide portion, in parallel through the reference and analyte waveguide portions, then through the outgoing waveguide portion, the analyte waveguide portion having an external surface that is functionalized relative to the reference waveguide portion so as to enable the external surface of the analyte portion to selectively interact with molecules of an analyte in a manner that imparts a phase change to the electromagnetic radiation passing through the analyte waveguide portion relative to the electromagnetic radiation passing through the reference waveguide portion sufficient to form an interference pattern correlating with the phase change.

3. A sensor comprising:
   (a) an optical waveguide comprising a material exhibiting an index of refraction to electromagnetic radiation, the optical waveguide comprising an incoming waveguide portion, a reference waveguide portion, an analyte waveguide portion, and an outgoing waveguide portion, the reference and analyte portions each having a first end coupled to the incoming waveguide portion and a second end coupled to the outgoing waveguide portion so as to conduct by total internal reflection electromagnetic radiation entering the incoming waveguide portion through the incoming waveguide portion, in parallel through the reference and analyte waveguide portions, then through the outgoing waveguide portion so as to form an interference pattern in the electromagnetic radiation passing through the outgoing waveguide portion, wherein the analyte waveguide portion has an external surface that is chemically functionalized relative to the reference waveguide portion so as to enable the analyte portion to selectively interact with molecules of an analyte in a manner that imparts a change to the electromagnetic radiation passing through the analyte waveguide portion relative to the electromagnetic radiation passing through the reference waveguide portion sufficient to cause a change in the interference pattern;
   (b) a source of electromagnetic radiation for introducing the electromagnetic radiation into the incoming waveguide portion; and
   (c) a detector for detecting the interference pattern.

4. A sensor comprising:
   (a) a first optical waveguide comprising a reference waveguide portion and an analyte waveguide portion both made of a material exhibiting an index of refraction to an electromagnetic radiation and both having a first end and a second end;
   (b) a second optical waveguide coupled to the first ends of the first optical waveguide for introducing the electromagnetic radiation into the first ends such that the electromagnetic radiation passes in parallel through the reference and analyte waveguide portions from the first ends to the second ends by total internal reflection;
   (c) a third optical waveguide coupled to the second ends of the first optical waveguide for converging the electromagnetic radiation at the second ends into a beam of the electromagnetic radiation that exhibits an interference pattern;
   (d) the analyte waveguide portion having an external surface that is chemically functionalized relative to the reference waveguide portion so as to enable the external surface of the analyte portion to selectively interact with molecules of an analyte in a manner that imparts a change to the electromagnetic radiation passing through the analyte waveguide portion relative to the electromagnetic radiation passing through the reference waveguide portion sufficient to cause a change in the interference pattern; and (e) a detector for detecting the change in the interference pattern.

5. A sensor comprising:

(a) a first optical waveguide made of a material exhibiting an index of refraction to an electromagnetic radiation, the first optical waveguide comprising an analyte waveguide portion and a reference waveguide portion each having first and second ends, the first optical waveguide being adapted to simultaneously conduct the electromagnetic radiation in parallel through the analyte waveguide portion and the reference waveguide portion from the first to the second ends, the analyte waveguide portion having an external surface that is functionalized relative to the reference waveguide portion so as to enable the external surface of the analyte waveguide portion to chemically react with molecules of an analyte;

(b) a radiation source adapted to produce the electromagnetic radiation and direct electromagnetic radiation into the first ends of the first optical waveguide for parallel passage of the electromagnetic radiation through the analyte waveguide portion and the reference waveguide portion from the first to the second ends;

(c) a second optical waveguide made of a material exhibiting an index of refraction to the electromagnetic radiation, the second optical waveguide being connected to the second ends of the analyte waveguide portion and the reference waveguide portion, the second optical waveguide serving to simultaneously conduct the electromagnetic radiation exiting the analyte and reference waveguide portions and thereby produce an interference pattern of the electromagnetic radiation, wherein interaction of the functionalized surface of the analyte waveguide portion with molecules of the analyte causes a change in the interference pattern; and (d) a detector optically coupled to the second optical waveguide so as to detect changes in the interference pattern.

6. A method for detecting molecules of an analyte, the method comprising:

(a) providing an optical waveguide having a reference waveguide portion, an analyte waveguide portion, and an outgoing waveguide portion, the optical waveguide being made of a material exhibiting an index of refraction to an electromagnetic radiation, the reference and analyte portions each having an end coupled to the outgoing waveguide portion so as to enable the optical waveguide to pass electromagnetic radiation simultaneously in parallel through the reference and analyte waveguide portions, then through the outgoing waveguide portion, the analyte waveguide portion having an external surface that is functionalized relative to the reference waveguide portion so as to enable the external surface of the analyte waveguide portion to selectively interact with molecules of an analyte;

(b) conducting electromagnetic radiation simultaneously in parallel through the reference and analyte waveguide portions into the outgoing waveguide portion so as to produce an interference pattern in the outgoing waveguide portion;

(c) contacting the external surface of the analyte waveguide portion with molecules of the analyte so as to allow molecules of the analyte to selectively interact with the functionalized surface, thereby causing a change in the electromagnetic radiation passing through the analyte waveguide portion relative to the reference waveguide portion sufficient to cause a change in the interference pattern; and (d) detecting the change in the interference pattern.

7. A sensor element according to claim 1 wherein the external surface of the analyte waveguide portion is functionalized by nitrene chemistry.

8. A sensor element, comprising:

(a) a reference waveguide portion having first and second ends and exhibiting an index of refraction to an electromagnetic radiation;

(b) an analyte waveguide portion having first and second ends and exhibiting an index of refraction to the electromagnetic radiation, the analyte waveguide portion having an external surface to which analyte-reactive functional groups have been covalently attached, the functional groups enabling analyte molecules to selectively attach to the analyte waveguide portion whenever the analyte waveguide portion is contacted with molecules of the analyte;

(c) means for introducing the electromagnetic radiation into the first ends of the reference waveguide portion and the analyte waveguide portion so as to cause each of the reference and analyte waveguide portions to internally conduct the electromagnetic radiation from the first ends to the second ends; and (d) electromagnetic radiation sensing means responsive to the electromagnetic radiation at the second ends of the reference and analyte waveguide portions, the electromagnetic radiation sensing means serving to detect a change in the electromagnetic radiation passing through the analyte waveguide portion, relative to the reference waveguide portion, resulting from attachment of analyte molecules to the analyte-reactive functional groups on the external surface of the analyte waveguide portion.

* * * * *